US010987059B2

(12) United States Patent
Dvir et al.

(10) Patent No.: US 10,987,059 B2
(45) Date of Patent: Apr. 27, 2021

(54) ELECTRONIC SCAFFOLD AND USES THEREOF

(71) Applicant: Ramot at Tel-Aviv University Ltd., Tel-Aviv (IL)

(72) Inventors: Tal Dvir, LeHavim (IL); Yosi Shacham-Diamand, Tel-Aviv (IL); Ron Feiner, Tel-Aviv (IL); Leeya Engel, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 765 days.

(21) Appl. No.: 15/037,129

(22) PCT Filed: Nov. 17, 2014

(86) PCT No.: PCT/IL2014/050994
§ 371 (c)(1),
(2) Date: May 17, 2016

(87) PCT Pub. No.: WO2015/071912
PCT Pub. Date: May 21, 2015

(65) Prior Publication Data
US 2016/0270729 A1    Sep. 22, 2016

Related U.S. Application Data

(60) Provisional application No. 61/905,230, filed on Nov. 17, 2013.

(51) Int. Cl.
*A61B 5/00*    (2006.01)
*A61N 1/05*    (2006.01)
(Continued)

(52) U.S. Cl.
CPC .............. *A61B 5/686* (2013.01); *A61B 5/287* (2021.01); *A61B 5/4848* (2013.01);
(Continued)

(58) Field of Classification Search
CPC ..... A61B 5/686; A61B 5/4848; A61B 5/6869; A61B 17/12181; A61F 2/24;
(Continued)

(56) References Cited

U.S. PATENT DOCUMENTS

| 5,843,134 A * | 12/1998 | Thong | A61M 5/1723 |
| | | | 607/17 |
| 6,600,956 B2 * | 7/2003 | Maschino | A61N 1/0556 |
| | | | 607/118 |

(Continued)

FOREIGN PATENT DOCUMENTS

| EP | 2229191 | 9/2010 |
| WO | WO 2005/007233 | 1/2005 |

(Continued)

OTHER PUBLICATIONS

Achyuta AK, Polikov VS, White AJ, Lewis HG, Murthy SK. Biocompatibility assessment of insulating silicone polymer coatings using an in vitro glial scar assay 2010. Macromol Biosci. 10(8):872-880.*

(Continued)

*Primary Examiner* — Linda C Dvorak
*Assistant Examiner* — Annabeth E Rodriguez

(57) ABSTRACT

A device comprising a three-dimensional polymeric element and an electronic element integrated with the polymeric element is disclosed. The electronic element is made up of one or more electrode(s) each individually connectable to a measuring device and/or a controller, and each independently having a thin electrically-isolating layer deposited thereon such that the electrode is exposed to an environment surrounding the electrode at one or more pre-determined locations over the electrode. The device can include cells and/or tissue and/or a therapeutically active agent incorporated within the polymeric material. Processes of fabricating (Continued)

the device, systems for operating the device and methods utilizing same are also disclosed.

20 Claims, 22 Drawing Sheets
(15 of 22 Drawing Sheet(s) Filed in Color)

(51) Int. Cl.
| | |
|---|---|
| A61N 1/362 | (2006.01) |
| A61N 1/39 | (2006.01) |
| A61L 27/36 | (2006.01) |
| A61F 2/24 | (2006.01) |
| C12N 5/077 | (2010.01) |
| C23C 14/34 | (2006.01) |
| C12N 5/00 | (2006.01) |
| A61B 5/287 | (2021.01) |
| A61K 35/34 | (2015.01) |

(52) U.S. Cl.
CPC .............. *A61B 5/6869* (2013.01); *A61F 2/24* (2013.01); *A61L 27/3604* (2013.01); *A61N 1/0563* (2013.01); *A61N 1/0587* (2013.01); *A61N 1/3621* (2013.01); *A61N 1/395* (2013.01); *C12N 5/0068* (2013.01); *C12N 5/0657* (2013.01); *C23C 14/34* (2013.01); *A61B 5/0031* (2013.01); *A61B 2562/164* (2013.01); *A61F 2002/249* (2013.01); *A61K 35/34* (2013.01); *A61L 2430/20* (2013.01); *C12N 2533/30* (2013.01)

(58) Field of Classification Search
CPC ... A61L 27/3604; A61L 27/36; A61N 1/0563; A61N 1/0587; A61N 1/3621; A61N 1/395
See application file for complete search history.

(56) References Cited

U.S. PATENT DOCUMENTS

| | | | |
|---|---|---|---|
| 2005/0013870 A1 | 1/2005 | Freyman et al. | |
| 2006/0136028 A1* | 6/2006 | Ross | A61N 1/0587 607/129 |
| 2007/0060815 A1* | 3/2007 | Martin | A61B 5/0408 600/372 |
| 2007/0219642 A1 | 9/2007 | Richter | |
| 2007/0248638 A1 | 10/2007 | Van Dyke et al. | |
| 2008/0096005 A1 | 4/2008 | Premasiri | |
| 2008/0208358 A1 | 8/2008 | Bellamkonda et al. | |
| 2008/0260831 A1 | 10/2008 | Badylak et al. | |
| 2009/0163990 A1 | 6/2009 | Yang et al. | |
| 2009/0248113 A1 | 10/2009 | Nimer et al. | |
| 2009/0280154 A1 | 11/2009 | Nielsen et al. | |
| 2010/0094110 A1* | 4/2010 | Heller | A61B 5/746 600/345 |
| 2010/0106233 A1 | 4/2010 | Grant et al. | |
| 2010/0114278 A1 | 5/2010 | McMorrow et al. | |
| 2010/0211172 A1* | 8/2010 | Bellamkonda | A61B 5/0031 623/11.11 |
| 2010/0255447 A1 | 10/2010 | Biris et al. | |
| 2010/0273667 A1 | 10/2010 | Kotov et al. | |
| 2011/0085968 A1 | 4/2011 | Jin et al. | |
| 2011/0087315 A1 | 4/2011 | Richardson-Burns et al. | |
| 2011/0143429 A1 | 6/2011 | Chun et al. | |
| 2012/0177910 A1 | 7/2012 | Weber et al. | |
| 2013/0085359 A1 | 4/2013 | Yao et al. | |
| 2014/0145365 A1* | 5/2014 | Omenetto | H01L 21/02 264/104 |
| 2014/0271784 A1 | 9/2014 | Yang et al. | |
| 2015/0202348 A1 | 7/2015 | Dvir et al. | |
| 2015/0202351 A1* | 7/2015 | Kaplan | A61B 5/6868 607/116 |
| 2016/0106886 A1 | 4/2016 | Dvir et al. | |
| 2018/0000990 A1 | 1/2018 | Dvir et al. | |
| 2018/0361023 A1 | 12/2018 | Dvir et al. | |
| 2020/0101198 A1 | 4/2020 | Dvir et al. | |

FOREIGN PATENT DOCUMENTS

| | | |
|---|---|---|
| WO | WO 2009/085547 | 7/2009 |
| WO | WO 2011/154424 | 12/2011 |
| WO | WO 2011/159923 | 12/2011 |
| WO | WO 2012/094208 | 7/2012 |
| WO | WO 2013/086502 | 6/2013 |
| WO | WO 2013/109642 | 7/2013 |
| WO | WO 2014/037942 | 3/2014 |
| WO | WO 2014/188420 | 11/2014 |
| WO | WO 2014/207744 | 12/2014 |
| WO | WO 2015/048136 | 4/2015 |
| WO | WO 2015/071912 | 5/2015 |
| WO | WO 2017/103930 | 6/2017 |

OTHER PUBLICATIONS

Official Action dated Jan. 10, 2019 From the US Patent and Trademark Office Re. U.S. Appl. No. 15/702,834. (19 pages).
International Preliminary Report on Patentability dated Dec. 3, 2015 From the International Bureau of WIPO Re. Application No. PCT/IL2014/050445.
International Preliminary Report on Patentability dated Jan. 7, 2016 From the International Bureau of WIPO Re. Application No. PCT/IL2014/050568.
International Search Report and the Written Opinion dated Apr. 4, 2017 From the International Searching Authority Re. Application No. PCT/IL2016/051344. (12 Pages).
International Search Report and the Written Opinion dated Aug. 18, 2014 From the International Searching Authority Re. Application No. PCT/IL2014/050445.
International Search Report and the Written Opinion dated Oct. 24, 2014 From the International Searching Authority Re. Application No. PCT/IL2014/050568.
Notice of Non-Compliant Amendment (37 CFR 1.121) dated May 5, 2015 From the US Patent and Trademark Office Re. U.S. Appl. No. 14/581,540.
Official Action dated Mar. 13, 2017 From the US Patent and Trademark Office Re. U.S. Appl. No. 14/581,540. (15 pages).
Official Action dated Jun. 28, 2016 From the US Patent and Trademark Office Re. U.S. Appl. No. 14/581,540.
Supplementary European Search Report and the European Search Opinion dated Nov. 28, 2016 From the European Patent Office Re. Application No. 14800309.8. (7 Pages).
Crapo et al. "An Overview of Tissue and Whole Organ Decellularization Processes", Biomaterials, 32(12): 3233-3243, Apr. 30, 2011.
Dvir et al. "Precascularization of Cardiac Patch on the Omentum Improves Its Therapeutic Outcome", Proc. Natl. Acad. Sci. USA, PNAS, 106(35): 14990-14995, Sep. 1, 2009.
Gilbert et al. "Decellularization of Tissues and Organs", Biomaterials, XP002730648, 27: 3675-3683, 2006. p. 3676, Para 2, Table 1, p. 3679, Para 3.
Homola "Surface Plasmon Resonance Sensors for Detection of Chemical and Biological Species", Chemical Reviews, 108(2): 462-493, Jan. 30, 2008.
Hsu et al. "Gold Nanoparticles Induce Surface Morphological Transformation in Polyurethane and Affect the Cellular Response", Biomacromolecules, 9(1): 241-248, Jan. 2008.
Johnson et al. "Tailoring Material Properties of a Nanofibrous Extracellular Matrix Derived Hydrogel", Nanotechnology, 22(49): 494015-1-494015-23, Published Online Nov. 21, 2011.
Porzionato et al. "Decellularization of Rat and Human Omentum to Develop Novel Scaffolds to Be Recellularized With Adipose Derived Stem Cells", Italian Journal of Anatomy and Embryology, IJAE, 116(1/Suppl.): 149, 2011.
Porzionato et al. "Decellularized Omentum as Novel Biologic Scaffold for Reconstructive Surgery and Regenerative Medicine", European Journal of Histpchemistry, 57(e4): 24-30, 2013.

(56) References Cited

OTHER PUBLICATIONS

Prabhakaran et al. "Electrospun Composite Scaffolds Containing Poly(Octanediol-CO-Citrate) for Cardiac Tissue Engineering", Biopolymers, 97(7): 529-538, Feb. 10, 2012.

Sawkins et al. "Hydrogels Derived From Demineralized and Decellularized Bone Extracellular Matrix", Acta Biomaterialia, 9: 7865-7873, 2013.

Shevach et al. "Fabrication of Omentum-Based Matrix for Engineering Vascularized Cardiac Tissues", Biofabrication, 6(2): 024101-1-024101-12, Published Online Jan. 24, 2014. Para 4.1, p. 9, Fig.8.

Shevach et al. "Omentum ECM-Based Hydrogel as a Platform for Cardiac Cell Delivery", Biomedical Materials, 10(3): 034106-1-034106-11, May 13, 2015. Para 2.1, p. 2, Fig.7.

Singelyn et al. "Catheter-Deliverable Hydrogel Derived From Decellularized Ventricular Extracellular Matrix Increases Endogenous Cardiomyocytes and Preserves Cardiac Function Post-Myocardial Infarction", Journal of the American College of Cardiology, JACC, 59(8): 751-763, Feb. 21, 2012.

Soffer-Tzur et al. "Optimizing the Biofabrication Process of Omentum-Based Scaffolds for Engineering Autologous Tissues", Biofabrication, 6(3): 035023-1-035023-14, Published Online Aug. 27, 2014. Table 1.

International Preliminary Report on Patentability dated May 26, 2016 From the International Bureau of WIPO Re. Application No. PCT/IL2014/050994.

International Search Report and the Written Opinion dated Mar. 22, 2015 From the International Searching Authority Re. Application No. PCT/IL2014/050994.

Aregueta-Robles et al. "Organic Electrode Coatings for Next-Generation Neural Interfaces", Frontiers in Neuroengineering, 7(Art. 15): 1-7, May 27, 2014. Abstract, Fig.1.

Cohen-Karni et al. "Nanocomposite Gold-Silk Nanofibers", Nano Letters, 12(10): 5403-5406, Aug. 28, 2012.

Dvir et al. "Activation of the ERK1/2 Cascade Via Pulsatile Interstitial Fluid Flow Promotes Cardiac Tissue Assembly", Tissue Engineering, 13(9): 2185-2193, Sep. 2007.

Dvir et al. "Nanowired Three-Dimensional Cardiac Patches", Nature Nanotechnology, 6: 720-725, Published Online Sep. 25, 2011.

Engelmayr Jr. et al. "Accordion-Like Honeycombs for Tissue Engineering of Cardiac Anisotropy", Nature Materials, 7(12): 1003-1010, Dec. 2008.

Fleischer et al. "Albumin Fiber Scaffolds for Engineering Functional Cardiac Tissues", Biotechnology and Bioengineering, 111(6): 1246-1257, Jun. 2014.

Fleischer et al. "Spring-Like Fibers for Cardiac Tissue Engineering", Biomaterials, 34(34): 8599-8606, Available Online Aug. 13, 2013.

Prabhakaran et al. "Electrospun Composite Scaffolds Containing Poly(Octanediol-CO-Citrate) for Cardiac Tissue Engineering", Biopolymers, 97(7): 529-538, Published Online Feb. 10, 2012.

Radisic et al. "Functional Assembly of Engineered Myocardium by Electrical Stimulation of Cardiac Myocytes Cultured on Scaffolds", Proc. Natl. Acad. Sci. USA, PNAS, 101(52): 18129-18134, Dec. 28, 2004.

Tian et al. "Macroporous Nanowire Nanoelectronic Scaffolds for Synthetic Tissues", Nature Materials, 11: 986-994, Nov. 2012 & Supplementary Information, p. 1-27, 2012.

Whelove et al. "Development and In Vitro Studies of a Polyethylene Terephthalate-Gold Nanoparticle Scaffold for Improved Biocompatibility", Journal of Biomedical Materials Research, Part B: Applied Biomaterials, 99B(1): 142-149, Published Online Jul. 28, 2011.

You et al. "Nanoengineering the Heart: Conductive Scaffolds Enhance Connexin 43 Expression", Nano Letters, 11(9): 3643-3648, Aug. 1, 2011.

Zimmermann et al. "Tissue Engineered of a Differential Cardiac Muscle Construct", Circulation Research, 90(2): 223-230, Feb. 8, 2002.

Supplementary European Search Report and the European Search Opinion dated Jun. 22, 2017 From the European Patent Office Re. Application No. 14862849.8. (12 Pages).

Official Action dated Jan. 4, 2019 From the US Patent and Trademark Office Re. U.S. Appl. No. 14/891,375. (15 pages).

Fleischer et al. "Coiled Fiber Scaffolds Embedded With Gold Nanoparticles Improve the Performance of Engineered Cardiac Tissues", Nanoscale, 6(16): 9410-9414, Aug. 21, 2014.

Shevach et al. "Gold Nanoparticle-Decellularized Matrix Hybrids for Cardiac Tissue Engineering", Nano Letters, 14(10): 5792-5796, Sep. 8, 2014.

Shevach et al. "Nanoengineering Gold Particle Composite Fibers for Cardiac Tissue Engineering", Journal of Materials Chemistry B, 1(39): 5110-5217, 2013.

"Neurite Development in PC12 Cells on Nanostructured Substrates", Advances in Science and Technology, 53: 85-90, Oct. 1, 2006.

Official Action dated Sep. 21, 2017 From the US Patent and Trademark Office Re. U.S. Appl. No. 14/891,375. (29 pages).

Official Action dated Mar. 8, 2018 From the US Patent and Trademark Office Re. U.S. Appl. No. 14/891,375. (16 pages).

Broda et al. "A Chemically Polymerized Electrically Conducting Composite of Polypyrrole Nanoparticles and Polyurethane for Tissue Engineering", Journal of Biomedical Materials Research, 98(4): 509-516, Sep. 15, 2011.

Official Action dated May 16, 2019 From the US Patent and Trademark Office Re. U.S. Appl. No. 15/702,834. (17 Pages).

Supplementary European Search Report and the European Search Opinion dated Jul. 22, 2019 From the European Patent Office Re. Application No. 16875065.1. (8 Pages).

Mao et al. "Recent Advances in Polymeric Microspheres for Parental Drug Delivery—Part 2", Expert Opinion on Drug Delivery, XP055605149, 9(10): 1209-1223, Aug. 28, 2012.

Yao et al. "Collagen Microsphere Serving as a Cell Carrier Supports Oligodendrocyte Progenitor Cell Growth and Differentiation for Neurite Myelination In Vivo", Stem Cell Research & Therapy, XP021162904, 4(5): 109-1-109-8, Sep. 9, 2013.

Official Action dated Dec. 27, 2019 From the US Patent and Trademark Office Re. U.S. Appl. No. 14/891,375. (32 pages).

Restriction Official Action dated Dec. 13, 2019 From the US Patent and Trademark Office Re. U.S. Appl. No. 16/061,675. (7 pages).

Merriam-Webster "Particle" Definition, Retrieved from www.merriam-webster.com, 1 Page, 2019.

Official Action dated May 22, 2020 from the US Patent and Trademark Office Re. U.S. Appl. No. 16/061,675. (32 pages).

Official Action dated Nov. 12, 2020 From the US Patent and Trademark Office Re. U.S. Appl. No. 16/061,675. (19 Pages).

Communication Pursuant to Article 94(3) EPC dated May 29, 2020 From the European Patent Office Re. Application No. 16875065.1. (8 Pages).

Collins et al. "The Poisson Distribution and Beyond: Methods for Microfluidic Droplet Production and Single Cell Encapsulation", Lab on A Chip, XP055426432, 15(17): 3439-3459, Published Online Jul. 30, 2015.

Final Official Action dated Oct. 16, 2020 From the US Patent and Trademark Office Re. U.S. Appl. No. 14/891,375. (19 pages).

\* cited by examiner

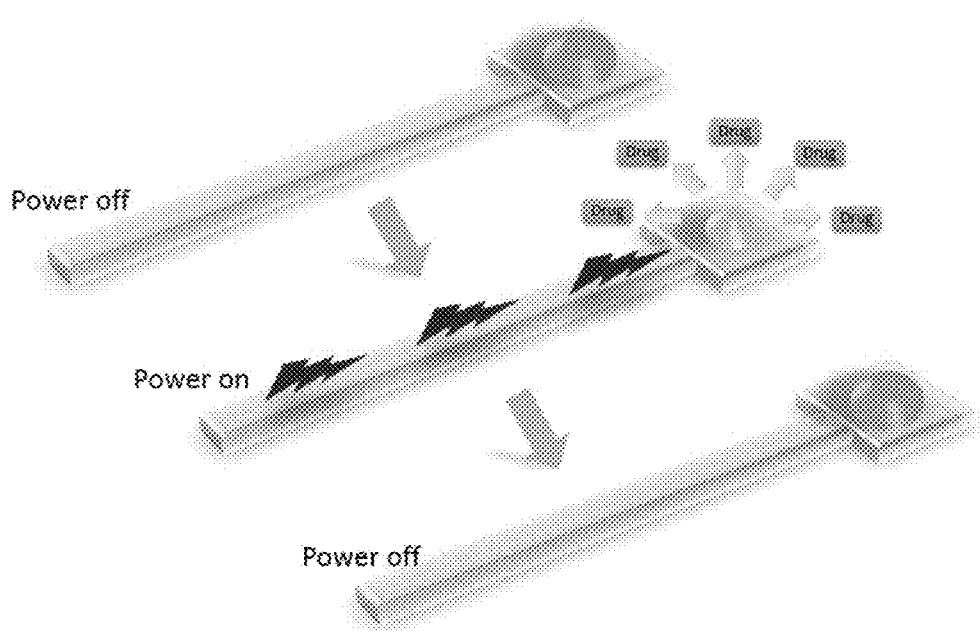
FIG. 14
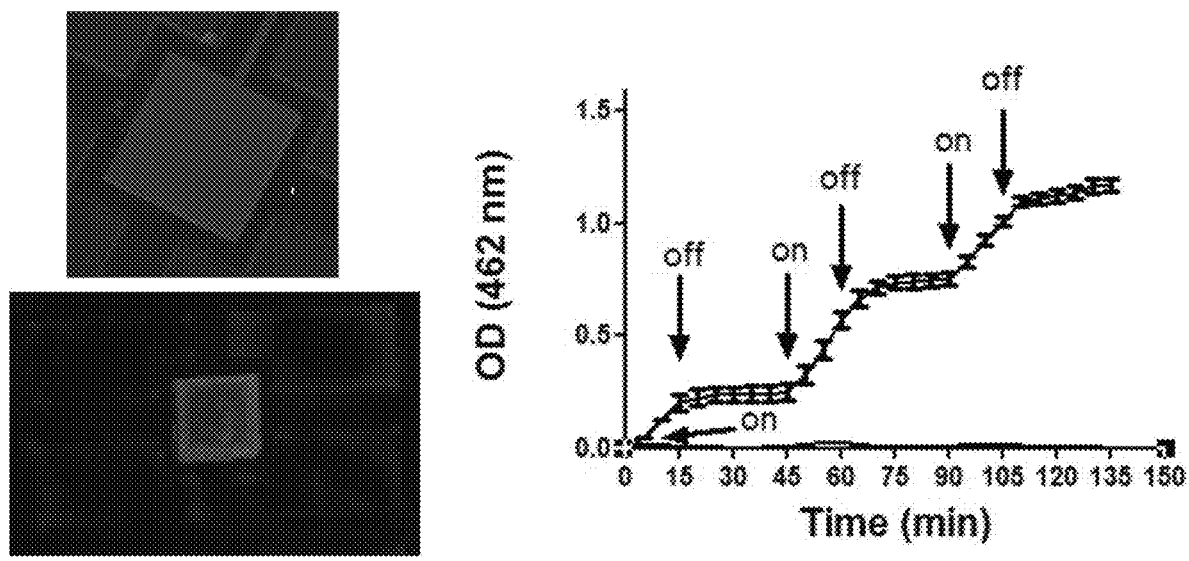
FIG. 15A
FIG. 15B

ELECTRONIC SCAFFOLD AND USES THEREOF

RELATED APPLICATIONS

This application is a National Phase of PCT Patent Application No. PCT/IL2014/050994 having International filing date of Nov. 17, 2014, which claims the benefit of priority under 35 USC § 119(e) of U.S. Provisional Patent Application No. 61/905,230 filed on Nov. 17, 2013. The contents of the above applications are all incorporated by reference as if fully set forth herein in their entirety.

FIELD AND BACKGROUND OF THE INVENTION

The present invention, in some embodiments thereof, relates to tissue engineering and, more particularly, but not exclusively, to an electronic scaffold, engineered tissue made therefrom and uses thereof.

About 8 million people in the United States suffer from a myocardial infarction (MI) during their lifetime, with about 800,000 new cases occurring each year. However, despite is prevalence, conventional therapies of MI remain limited by the inability of the myocardium to regenerate after injury and the shortage of donor organs that are available for transplantation. MI therefore continues to be a degenerative disease with a peak of cell death occurring at the onset of the infarction and also continuing thereafter. Cell-based therapies or tissue engineering approaches have been recognized as viable approaches to improve healing after a MI and restore the function of cardiac tissue.

Cardiac tissue engineering (CTE) has emerged as a promising treatment for replacing the scar tissue formed after myocardial infarction. Engineered cardiac patches to replace scar tissue after myocardial infarction can be produced by seeding cardiac cells within porous three dimensional ("3D") biomaterials, which provide mechanical support while cells organize into a functioning tissue.

Improving the viability, ultrastructural morphology and functionality of engineered cardiac tissue has been addressed by growing cell constructs in advanced bioreactors providing high mass transfer or exposing the tissues to electrical (Radisic, M et al. Pro. Na. Acad. Sci. USA 101, 18129-18134 (2004)) and mechanical cues (Zimmermann, W. H., et al. Circ. Res. 90, 223-230 (2002); Dvir, et al. Tissue Eng. 13, 2185-2193 (2007)). Scaffold structural and mechanical properties can be improved by microfabrication processes that provide controllable stiffness and anisotropy (Engelmayr, G. C., et al. Nature Mat. 7, 1003-1010 (2008)).

WO 2012/194208 discloses incorporating electrically conductive nanowires within scaffolds, to enhance tissue growth, bridge the electrically resistant pore walls and improve electrical communication between adjacent cardiac cell bundles.

WO 2013/109642 discloses a nanofiber structure featuring a basketweave configuration, which is made by electrospinning a biodegradable polymer and weaving strips of the electrospun nanofibers.

Dvir et al., 2011, Nature nanotechnology 6, 720-725, teaches embedding of gold nanowires within the pore walls of macroporous alginate scaffolds to increase the spatial and overall conductivity of the matrix. When cardiac cells were cultured in these nanowired scaffolds they exhibited increased expression of contractile and electrical coupling proteins.

You et al, 2011, Nano letters 11, 3643-3648 teaches cardiomyocytes cultured in hybrid hydrogel scaffolds based on spherical gold NPs, homogeneously distributed throughout a polymeric gel. The cells exhibited increased expression of connexin 43, a protein located between cardiac cells, responsible for electrical signal transfer. Additional background art includes Tian et al., Nature Materials, Vol. 11, November 2012, pp. 986-994; Fleischer et al., Biotechnology and Bioengineering Volume 111, Issue 6, pages 1246-1257, June 2014; WO 2005/007233; PCT/IL2014/050445; Prabhakaran et al., 2011, Journal of nanoscience and nanotechnology 11, 3039-3057; Whelove et al., 2011, J Biomed Mater Res Part B 2011:99B:142-149; Karni et al., Nano letters, 2012, 12(10), 5403-5406; Shan-hui Hsu Biomacromolecules 2008, 9, 241-248; Prabhakaran et al., 2012, Biopolymers Volume 97, 7, pages 529-538; Fleischer et al., Biomaterials, 2013, 34(34), 8599-8606; and U.S. Patent Application having Publication No. 20100106233.

Currently known methodologies of CTE are limited by the inability to monitor and control the engineered tissue's performance after transplantation.

SUMMARY OF THE INVENTION

The present invention, in some embodiments thereof, relates to tissue engineering and, more particularly, but not exclusively, to an electronic scaffold, engineered tissue made therefrom and uses thereof.

The present invention, in some embodiments thereof, relates to a scaffold device comprising a scaffold element made of a polymeric material (three-dimensional polymeric element), integrating an electronic element (e.g., a microelectronic element), to an engineered tissue made therefrom by incorporating and cultivating cells in the scaffold element, to systems for operating the device and/or the engineered tissue and to utilizing the device and/or the engineered tissue, optionally be means of the disclosed system, in monitoring (e.g., recording) function and/or activity (e.g., electrical activity) of a cell or a tissue; in stimulating a function and/or activity (e.g., electrical activity) of a cell or a tissue; in effecting and/or controlling drug release from the device and/or engineered tissue; and in studying the effect (e.g., toxicity or efficacy) of a drug on a cell or a tissue.

According to an aspect of some embodiments of the present invention there is provided a scaffold device comprising: a three-dimensional polymeric element (a scaffold element); and an electronic element being integrated with (or being in contact with) the polymeric element, the electronic element comprising at least one electrode being connectable to a measuring device and/or a controller, the electrode having an electrically-isolating layer deposited thereon such that a portion of the electrode remains partially uncoated in at least one location and is exposed to an environment surrounding the electrode at the at least one location.

According to some embodiments of the present invention, the electrode is exposed to the environment at a tip of the electrode.

According to some embodiments of the present invention, the electrode is exposed to the environment at a plurality of discrete locations over the electrode.

According to some of any of the embodiments of the present invention, the thin electrically-isolating layer is an electrically-isolating polymeric layer.

According to some of any of the embodiments of the present invention, the electrically-isolating polymeric layer comprises an epoxy photoresist and/or a polyimide.

According to some of any of the embodiments of the present invention, the thin electrically-isolating layer has a thickness that ranges from 0.1 micron to 100 microns.

According to some of any of the embodiments of the present invention, at least one dimension of the electrode ranges from 1 micron to 1000 microns.

According to some of any of the embodiments of the present invention, the at least one electrode has a shape of a straight line.

According to some of any of the embodiments of the present invention, the at least one electrode has a shape of a curved line.

According to some of any of the embodiments of the present invention, the at least one electrode is elastic.

According to some of any of the embodiments of the present invention, the at least one electrode has a generally constant conductivity as a function of a strain exhibited by the at least one electrode.

According to some of any of the embodiments of the present invention, the electronic element comprises a plurality of electrodes, each being individually connectable to a measuring device and/or a controller, and each independently having a thin electrically-isolating layer deposited thereon such that a portion of the electrode remains partially uncoated in at least one location and is exposed to the environment surrounding the electrode at the at least one location.

According to some of any of the embodiments of the present invention, the controller is configured for transmitting stimulation signals through the electrode.

According to some of any of the embodiments of the present invention, the device further comprises a miniature power source mounted in proximity to the electronic element.

According to some of any of the embodiments of the present invention, the measuring device is configured for measuring signals transmitted from the polymeric element through the electrode.

According to some of any of the embodiments of the present invention, the measuring device is configured for measuring signals transmitted from the environment through the electrode.

According to some of any of the embodiments of the present invention, the polymeric element comprises an electrospun fibrous polymeric material.

According to some of any of the embodiments of the present invention, the polymeric material comprises at least one of albumin, a polycaprolactone (PCL), gelatin, a poly (lactic acid) (PLA), a poly(lactic acid-co-glycolic acid) (PLGA), decellularized extracellular matrix and any combination thereof.

According to some of any of the embodiments of the present invention, polymeric material comprises a polycaprolactone (PCL) and gelatin.

According to some of any of the embodiments of the present invention, the polymeric material comprises albumin.

According to some of any of the embodiments of the present invention, the polymeric element comprises an electro-responsive polymeric material.

According to some of any of the embodiments of the present invention, the device further comprises cells incorporated in and/or on the polymeric element.

According to some of any of the embodiments of the present invention, the cells form a tissue.

According to some of any of the embodiments of the present invention, the device further comprises a therapeutically active agent incorporated in and/or on the polymeric element.

According to some of any of the embodiments of the present invention, the polymeric element comprises an electro-responsive polymer and a therapeutically active agent is associated with the electro-responsive polymeric material via electrostatic interactions.

According to some of any of the embodiments of the present invention, a scaffold device as described herein is usable for being implanted in or on a tissue or an organ of a subject in need thereof.

According to some of any of the embodiments of the present invention, a scaffold device as described herein is usable for monitoring and/or stimulating an activity and/or a function of a cell and/or a tissue.

According to some of any of the embodiments of the present invention, the cell or the tissue is incorporated in the polymeric element.

According to some of any of the embodiments of the present invention, the scaffold device as described herein is usable for monitoring and/or stimulating an activity and/or a function of the cell or the tissue in vivo.

According to some of any of the embodiments of the present invention, a scaffold device as described herein is usable for controlling a release of a therapeutically active agent from a polymeric element.

According to some of any of the embodiments of the present invention, a scaffold device as described herein is usable for determining a toxicity or an efficacy of a therapeutically active agent to a cell or tissue.

According to some of any of the embodiments of the present invention, the determining comprises: providing a device comprising a therapeutically active agent as described herein, in which a cell or a tissue is incorporated in the polymeric element; monitoring a function or activity of a cell or a tissue incorporated in the polymeric element; and comparing the monitored function or activity of the cell or the tissue with a function or activity of the cell or the tissue without a therapeutically active agent, thereby determining a toxicity or an efficacy of the therapeutically active agent to the cell or the tissue.

According to an aspect of some embodiments of the present invention there is provided a method of determining a toxicity or an efficacy of a therapeutically active agent to a cell or tissue, wherein the determining is effected as described herein.

According to an aspect of some embodiments of the present invention there is provided a system comprising the device as described in any one of the embodiments herein, and any combination thereof, and at least one electric device selected from the group consisting of a controller and a measuring device.

According to an aspect of some embodiments of the present invention there is provided a method of implantation, comprising: implanting a scaffold device comprising a cell or a tissue associated with the scaffold element, as described herein in any one of the respective embodiments, in an organ; and receiving electrical signals from the cells via the electronic element.

According to some of any of the embodiments of the present invention, the scaffold device further comprises a therapeutically active agent incorporated in the polymeric element, the method comprising transmitting stimulating signals via the electronic element so as to controllably release the therapeutically active agent from the polymeric element.

According to some of any of the embodiments of the present invention, the cells are responsive to electrical stimulation and the method comprising transmitting stimulating signals via the electronic element so as to stimulate the cells.

According to an aspect of some embodiments of the present invention there is provided a method of implantation, comprising: implanting a scaffold device in an organ, the scaffold device comprising a therapeutically active agent, as described in any one of the respective embodiments; and transmitting stimulating signals via the electronic element so as to controllably release the therapeutically active agent from the polymeric element.

According to an aspect of some embodiments of the present invention there is provided a method of implantation, comprising: implanting a scaffold device in an organ, the scaffold device comprising a cell or a tissue is association with the scaffold element, as described herein in any one of the respective embodiments, wherein the cells are responsive to electrical stimulation; and transmitting stimulating signals via the electronic element so as to stimulate the cells.

According to some of any of the embodiments of the present invention, the cells are cardiac cells and the organ is a myocardium.

According to some of any of the embodiments of the present invention, the signals are selected for pacing the myocardium.

According to some of any of the embodiments of the present invention, the cells are liver cells and the organ is a liver.

According to an aspect of some embodiments of the present invention there is provided a method of treating a disease or disorder caused by dysfunction in, or damage to, an excitable tissue in a subject in need thereof, the method comprising transplanting a scaffold device comprising a cell and/or a tissue and/or a therapeutically active agent, as described herein in any one of the respective embodiments, in the subject.

According to an aspect of some embodiments of the present invention there is provided a scaffold device a described herein, for use in a method of treating a disease or disorder, as described herein in any one of the respective embodiments, and any combination thereof.

According to some of any of the embodiments of the present invention, the disorder is a cardiac disorder associated with a defective or absent myocardium, and/or characterized by abnormal cardiac rhythm.

According to further aspects of some embodiments of the present invention, there are provided uses of a scaffold device as described herein, in any one of the methods as described herein, and any respective embodiment or combination of embodiments thereof.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
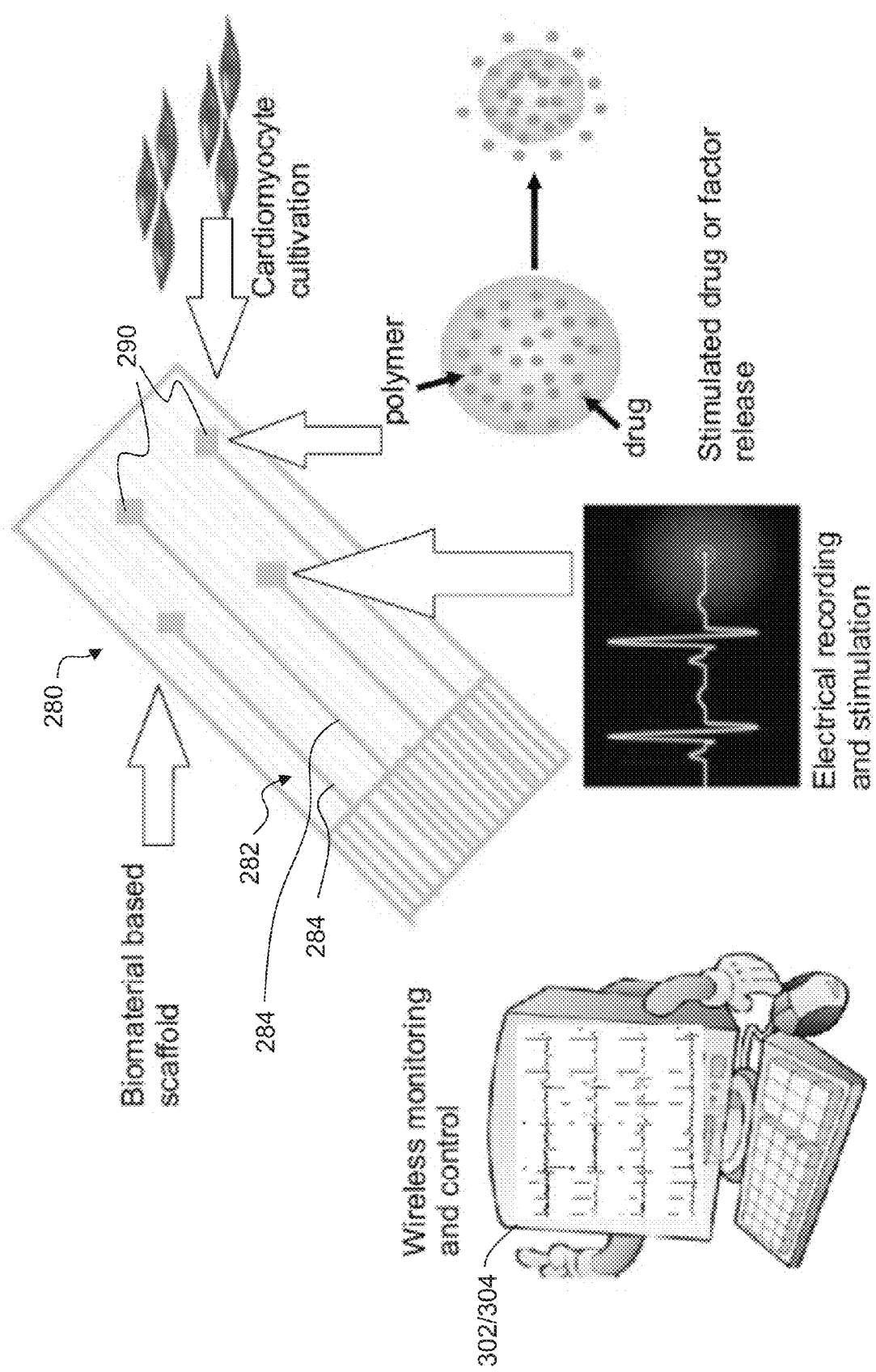
Figure 1B:
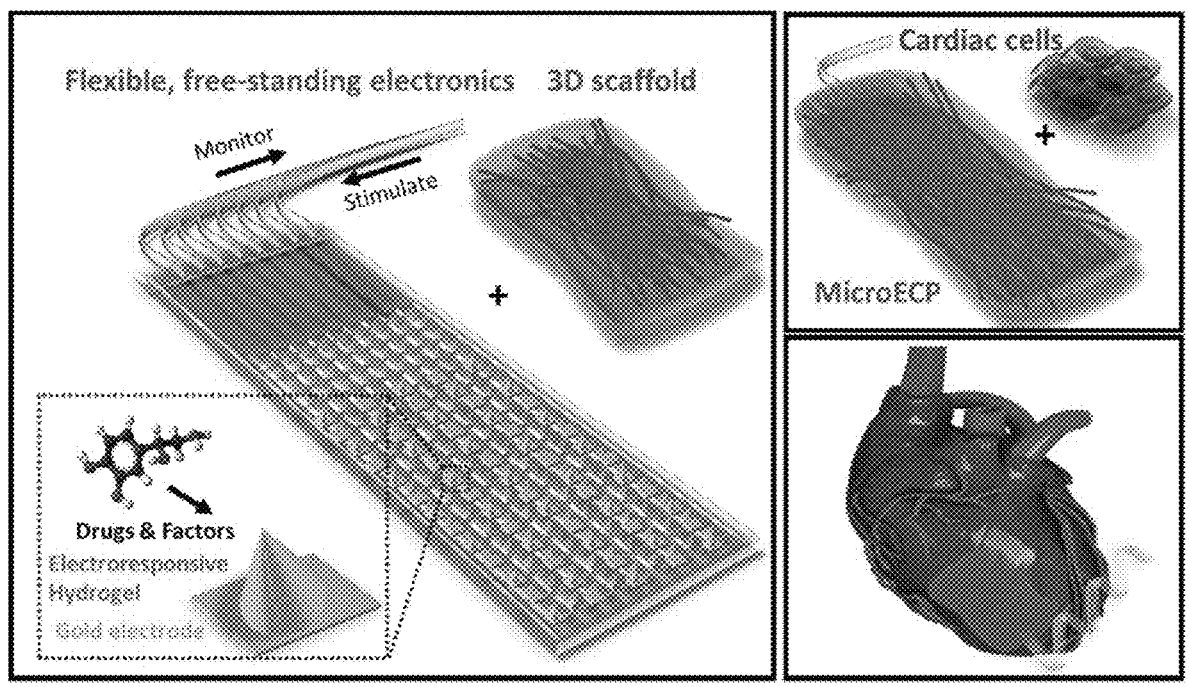

FIGS. 1A-B present schematic illustrations describing an operation principle of an exemplary system according to some embodiments of the present invention (FIG. 1A) and an exemplary scaffold device according to some embodiments of the present invention (FIG. 1B), comprised of e.g., gold electrodes having deposited thereon electro-responsive polymeric material loaded with one or more therapeutically active agent(s) (e.g., drug and/or growth factors) and integrated with a 3D scaffold element (left illustration), whereby cardiac cells are associated with the scaffold element, as depicted in the top right illustration, and the entire device is engaged with the heart as a cardiac patch (bottom right illustration).

Figures 2A, 2B:
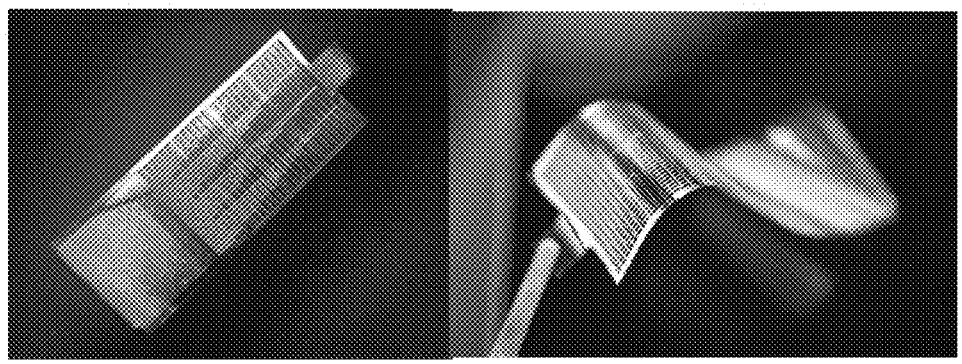

FIGS. 2A-B present photographs of an exemplary electronic element of a device according to some embodiments of the invention, made of a gold electrode and a SU-8-based polymeric layer, released from the wafer utilized in its preparation, and before integration with a scaffold element to form the device.

Figure 3:
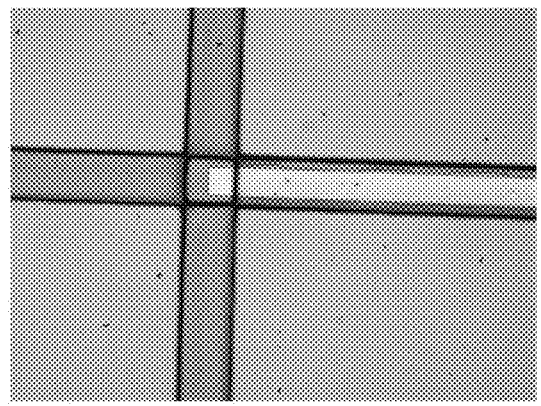

FIG. 3 presents a microscope image of an exposed tip of a gold electrode in an electronic element as described in FIGS. 2A-B, according to exemplary embodiment of the present invention.

Figure 4:
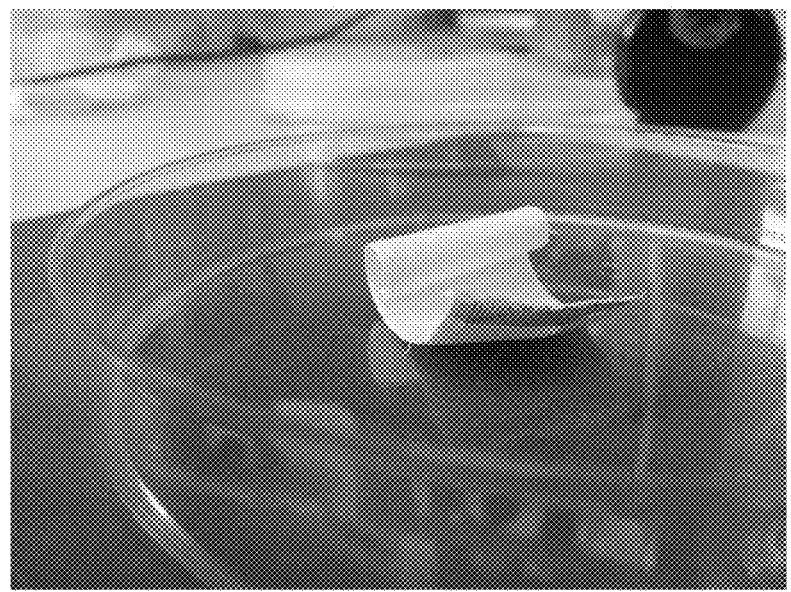

FIG. 4 presents an image of an exemplary device according to some embodiments of the present invention after depositing on the electronic element PCL/Gelatin nanofibers by electro spinning.

Figure 5A:
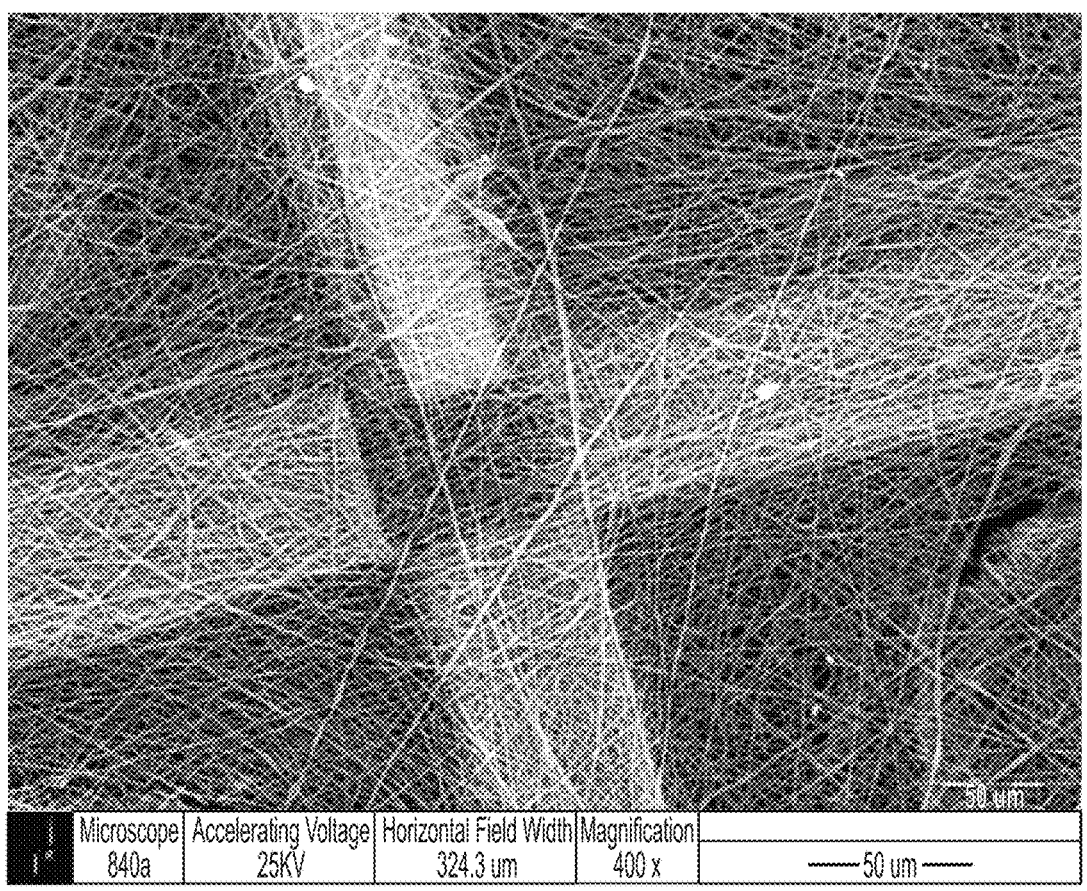
Figure 5B:
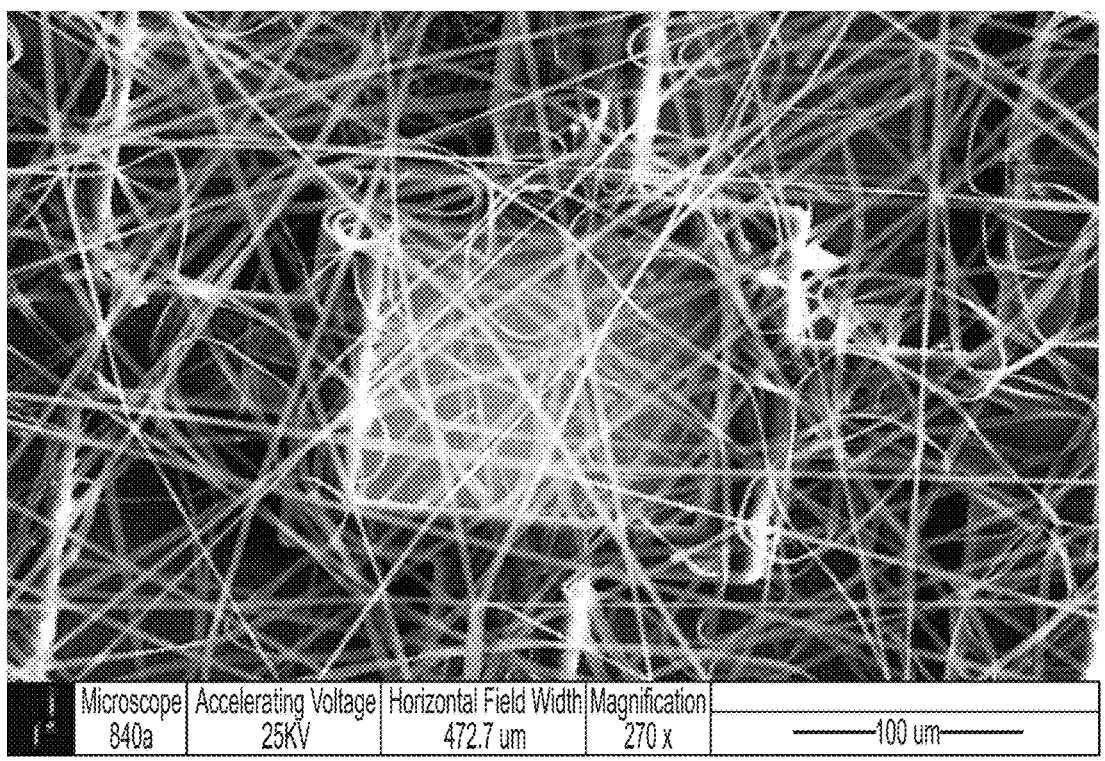

FIGS. 5A-B presents scanning electron micrographs (SEMs) of exemplary devices according to some embodiments of the present invention, showing a gold electrode coated by a SU-8-based polymeric layer and covered by PCL/gelatin fibrous scaffold element (FIG. 5A) and by albumin fibrous scaffold element (FIG. 5B).

Figure 6:
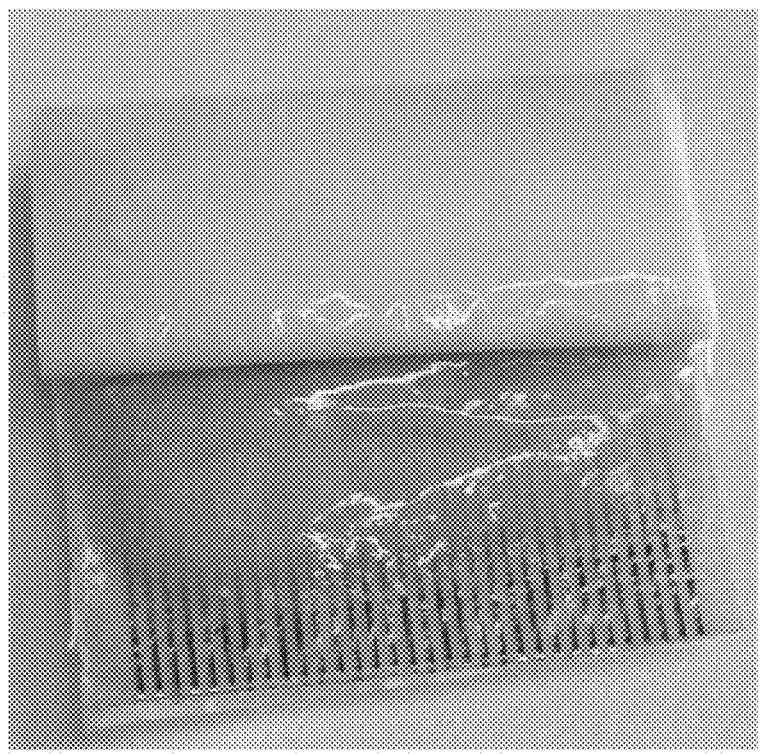

FIG. 6 presents an image of an exemplary device comprising an electronic element and PCL/gelatin scaffold and seeded with cardiomyocytes.

Figure 7A:
Figure 7B:
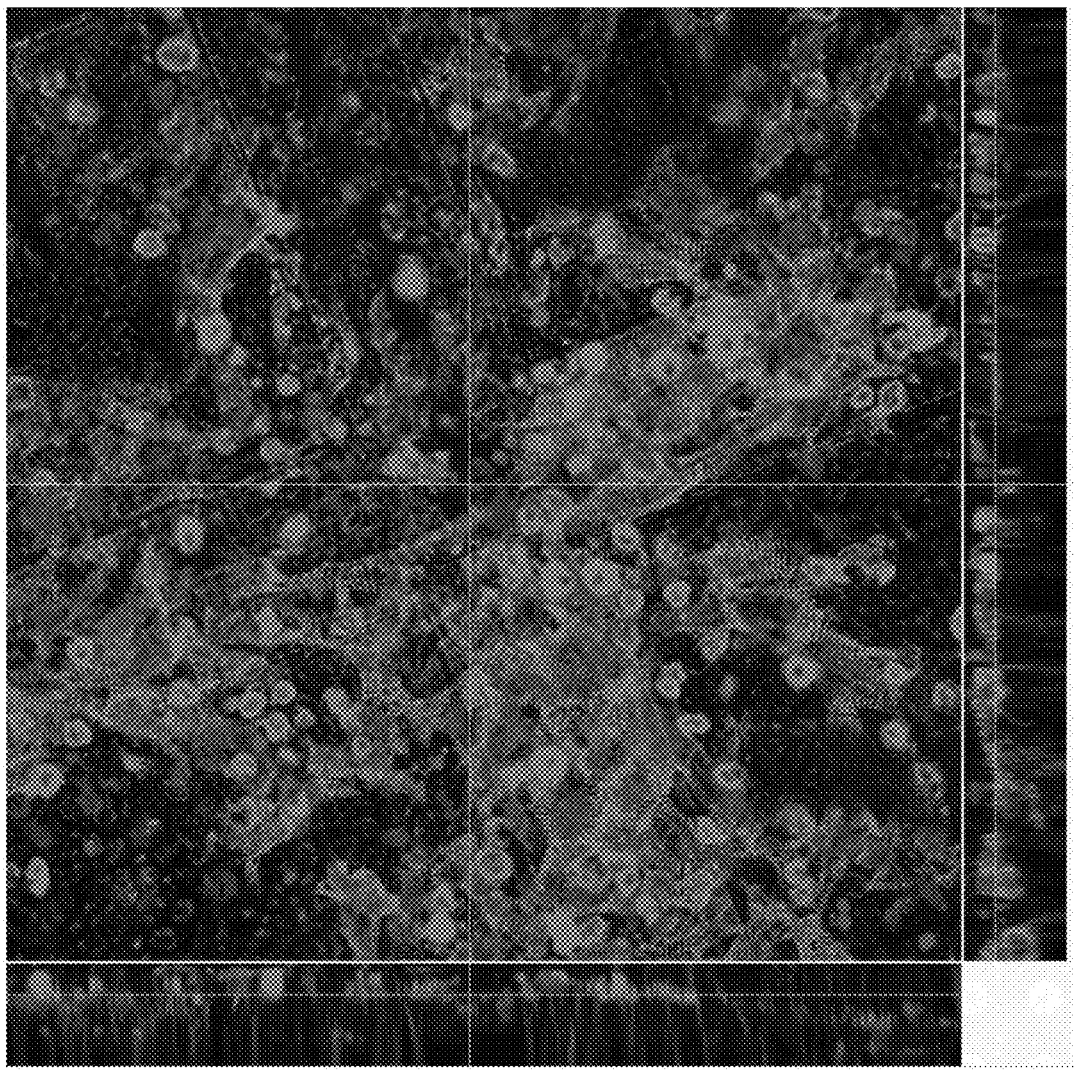

FIGS. 7A-B present a fluorescent microscope image of rat neonatal ventricular cardiomyocytes seeded on a device as presented in FIGS. 5A and 6 (FIG. 7A) and on a device as presented in FIG. 5B (FIG. 7B).

Figure 8:
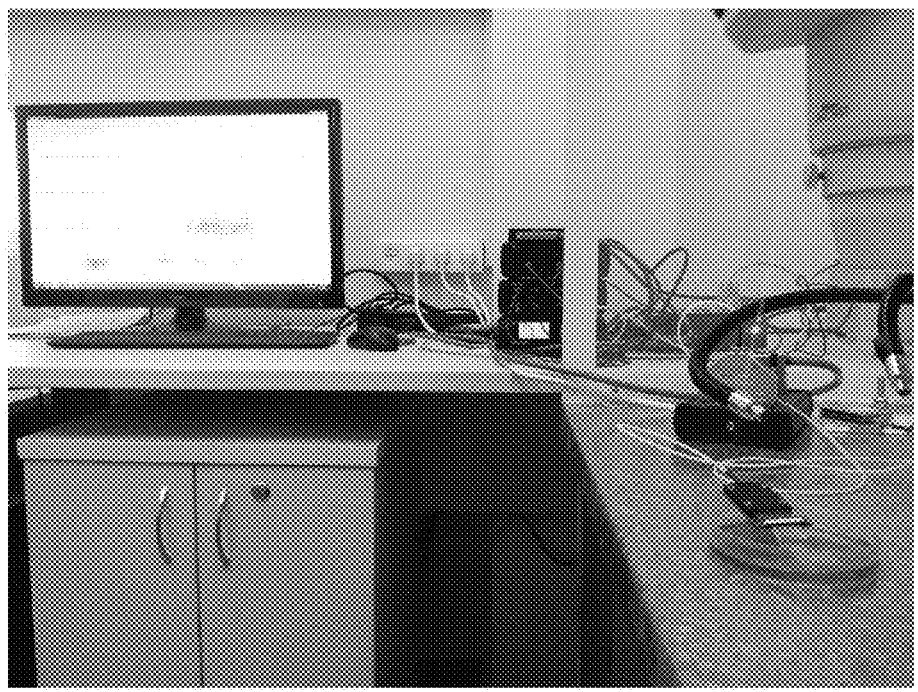

FIG. 8 presents an exemplary system set up for electrical signal readings using a device according to some embodiments of the present invention.

Figure 9:
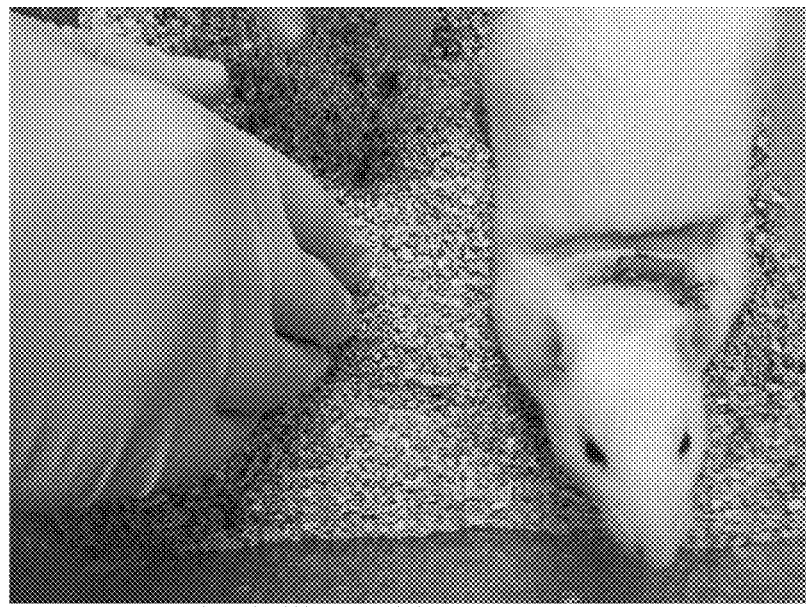

FIG. 9 is a photograph showing subcutaneous implantation of an engineered (cyborg) tissue according to some embodiments of the present invention into a Sprague-Dawly rat.

Figure 10:

FIG. 10 is a photograph showing recording action potentials and actuating the implanted engineered (cyborg) tissue, upon sedating the animal and connecting it to a pre-amplifier.

Figure 11A:
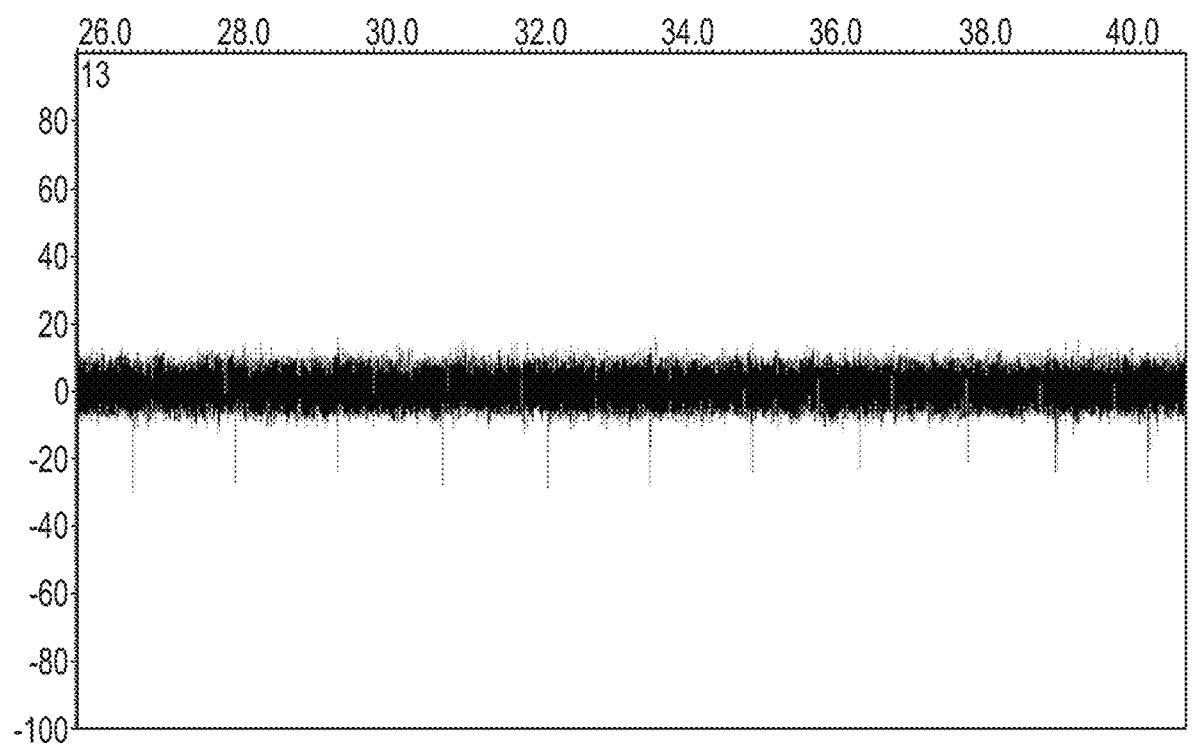
Figure 11B:
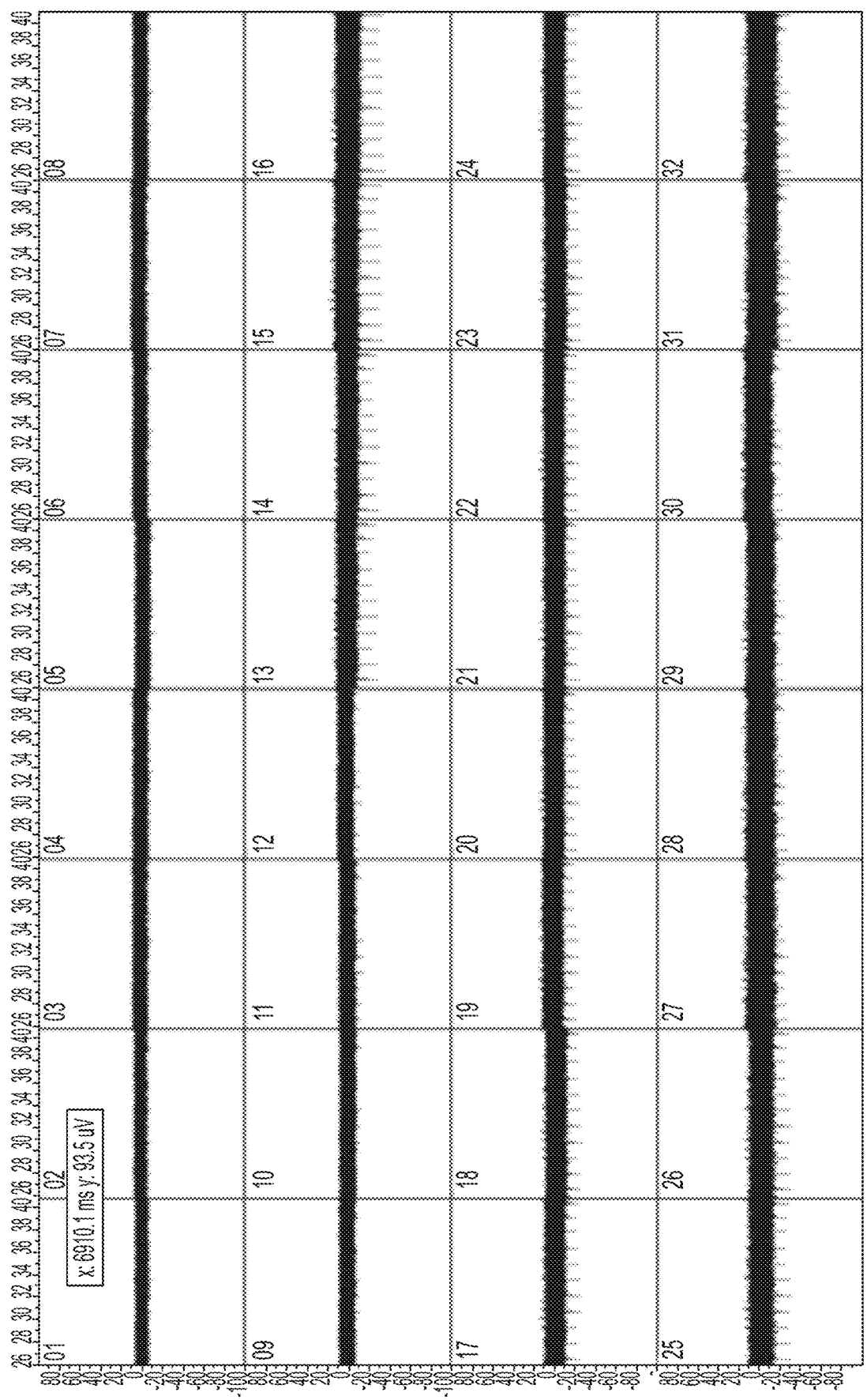

FIGS. 11A-B present action potentials recorded from a single (FIG. 11A) and multiple (FIG. 11B) electrodes in an in vitro experiment using an exemplary engineered (cyborg) tissue according to some embodiments of the present invention, as presented in FIG. 7B.

Figure 12:
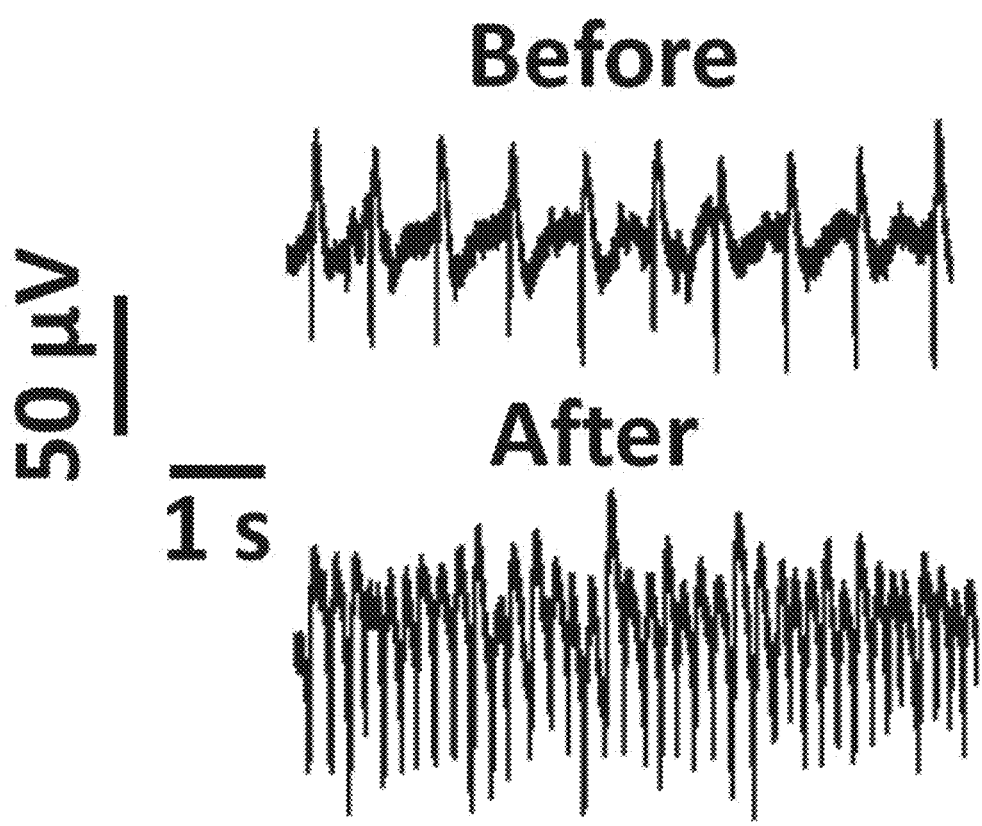

FIG. 12 presents action potentials recorded from a single electrode of a device cultured with neonatal rat ventricular cardiomyocytes, as presented in FIG. 7B, before (top) and after (bottom) adding a stimulating drug (Noradrenalin).

Figure 13A:
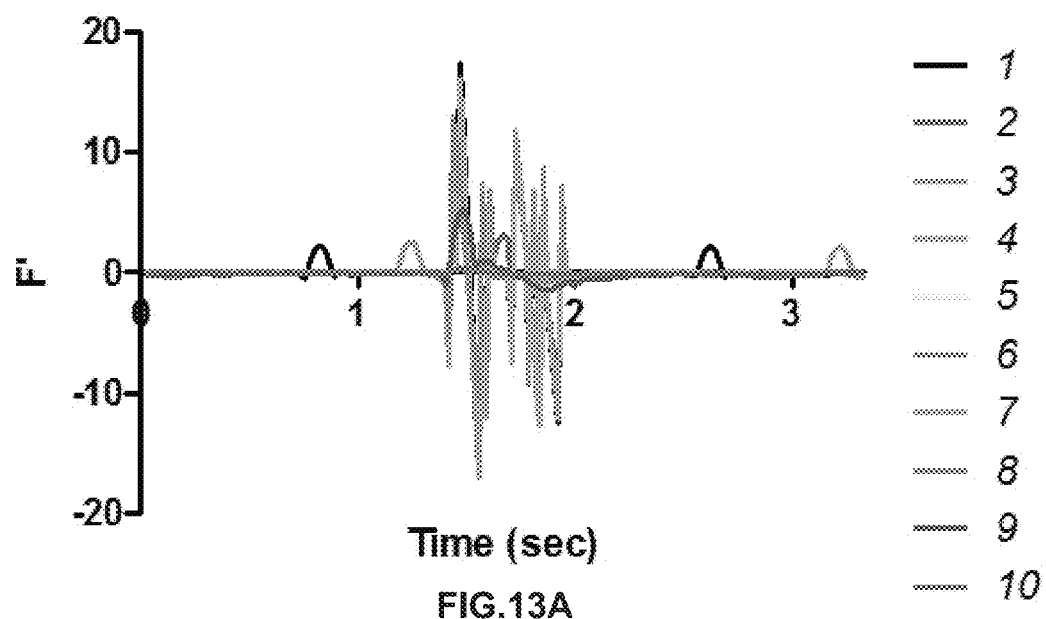
Figure 13B:
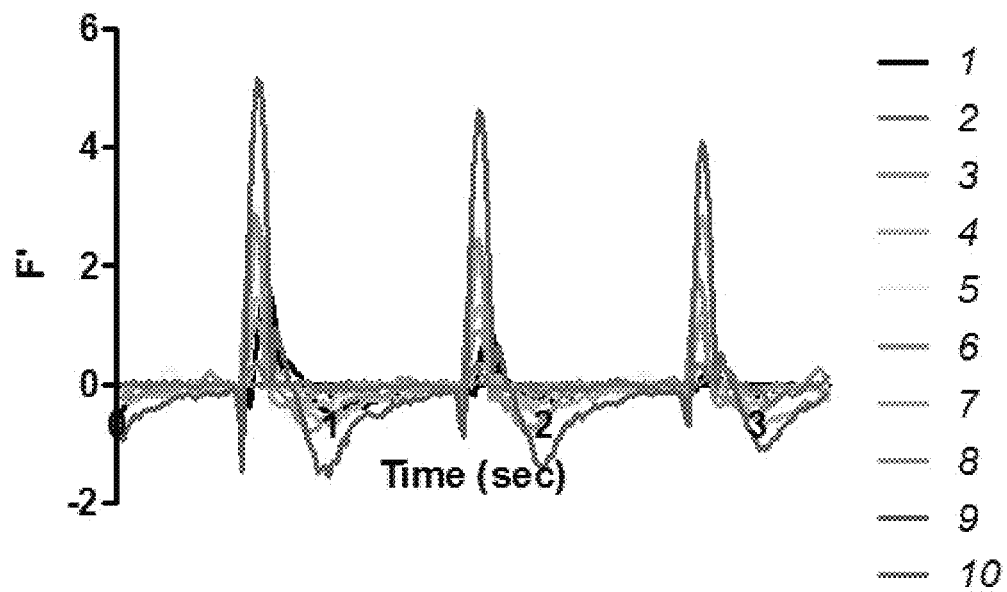

FIGS. 13A-B present the data obtained in measurements for evaluating the influence of electrical stimulation from a device as presented in FIG. 7B, incubated with a fluorescent calcium probe that fluoresces when the tissue contracts, showing images of the tissue before stimulation (FIG. 13A) and after the tissue was stimulated at a 1 Hz pace from within the device (FIG. 13B).

FIG. 14 presents a schematic illustration of a device, according to some embodiments of the present invention, in which the three dimensional polymeric element is formed from an electro-responsive polymer, which has a drug bound thereto via electrostatic interactions, whereby the drug is released when electric power (e.g., potential) is applied.

FIGS. 15A-B present a SEM image of an exemplary bare electronic element according to the present embodiments before (top image) and an image obtained by fluorescent microscopy (bottom image) after deposition of PolyAMPS-containing co-polymer loaded with Fluorescein (FIG. 15A), and a graph showing a release profile of dopamine from a PolyAMPS-containing scaffold, as measured by optical density (FIG. 15B).

Figure 16:
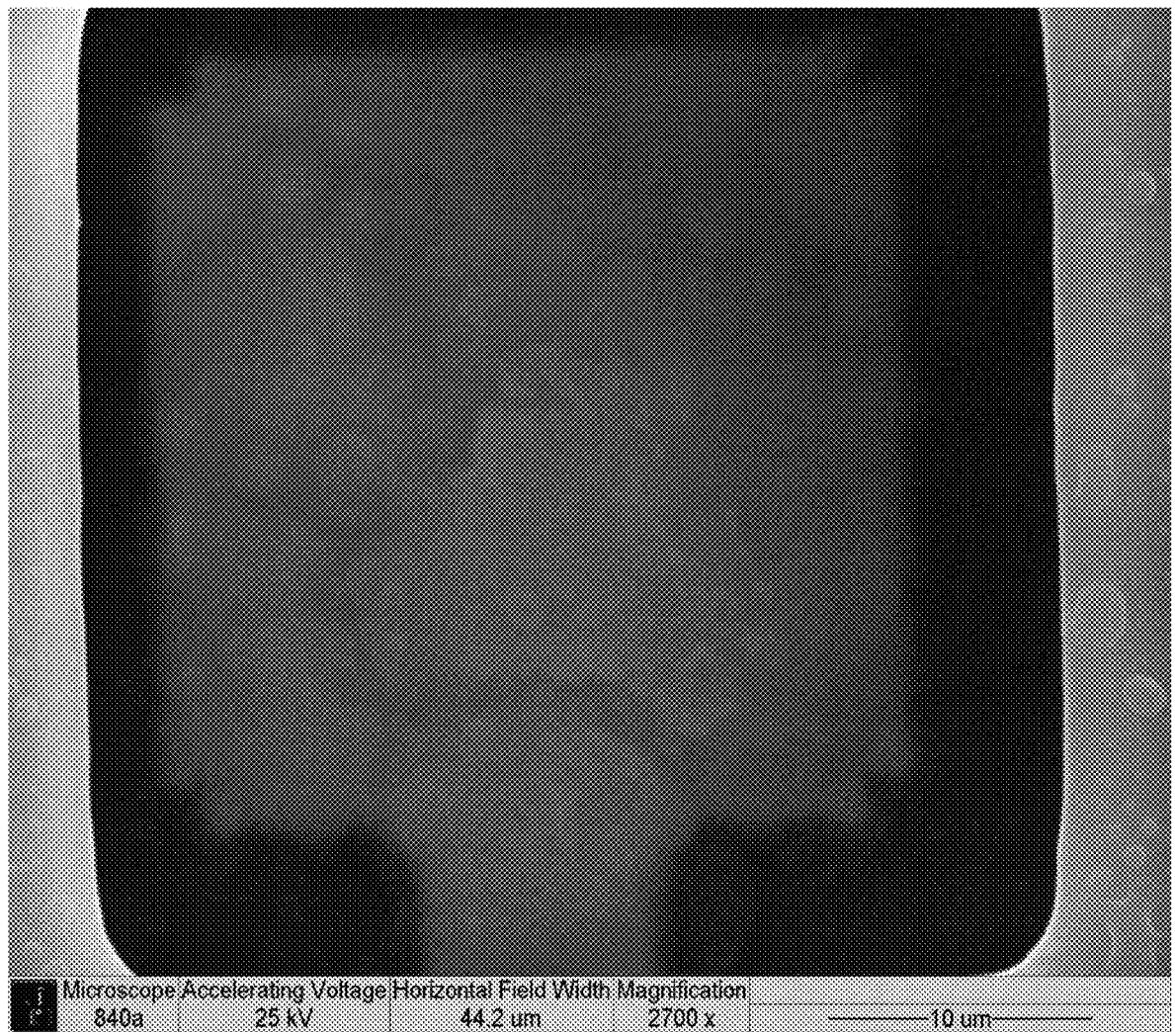

FIG. 16 presents a scanning electron micrograph (SEM) of a polypyrrole hydrogel deposited on a gold electrode having a TiN layer.

Figure 17:
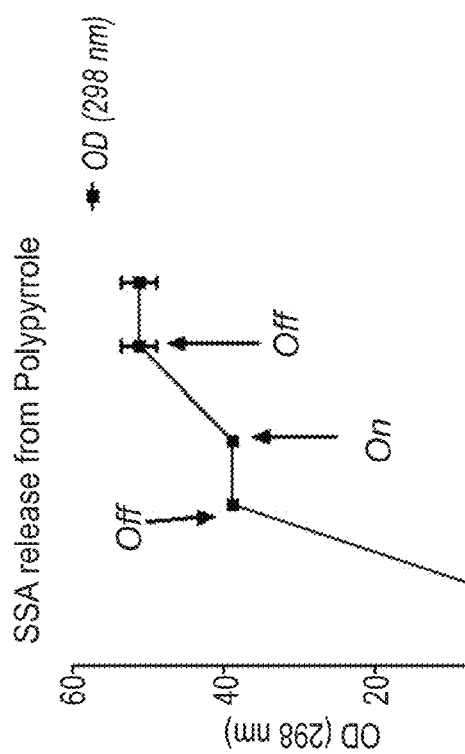

FIG. 17 presents a graph showing the release profile of SSA from a polypyrrole hydrogel, upon application of electrical power (on).

Figure 18:
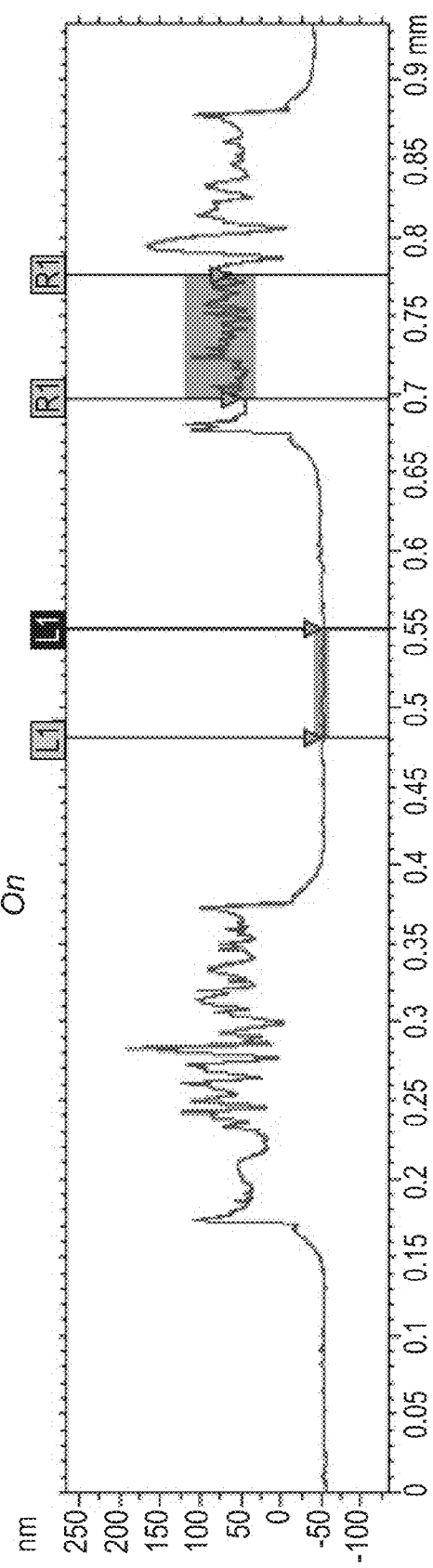

FIG. 18 presents a profile measurement of TiN layer deposited on gold electrodes, according to exemplary embodiments of the present invention.

Figure 19:
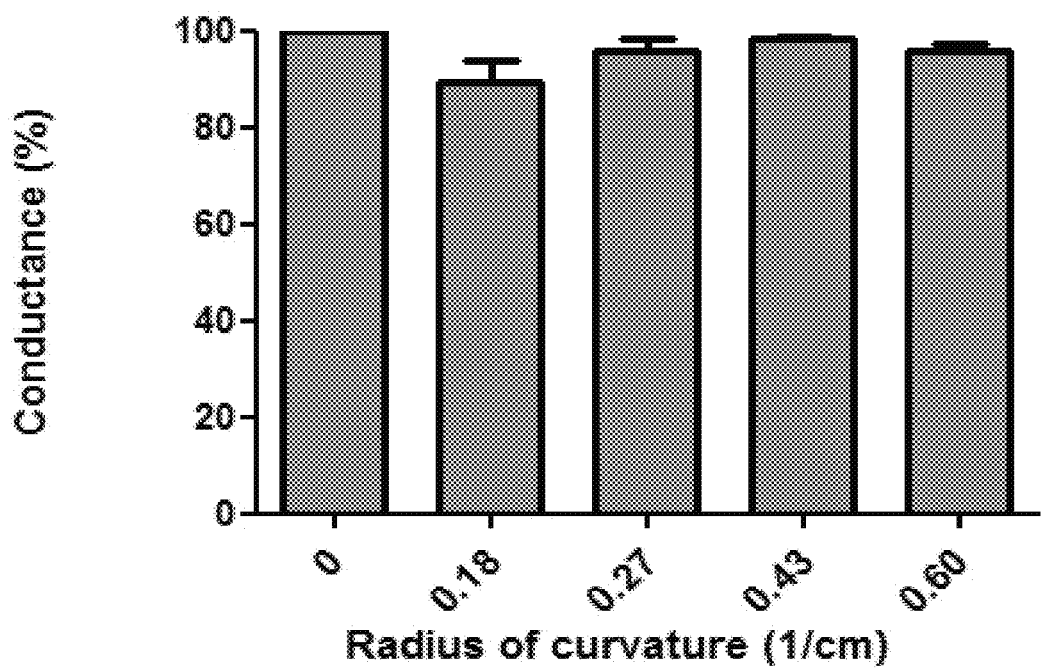

FIG. 19 is a bar graph showing the conductance of an exemplary electronic element according to some embodiments of the present invention, as a function of the radius of curvature.

Figure 20:
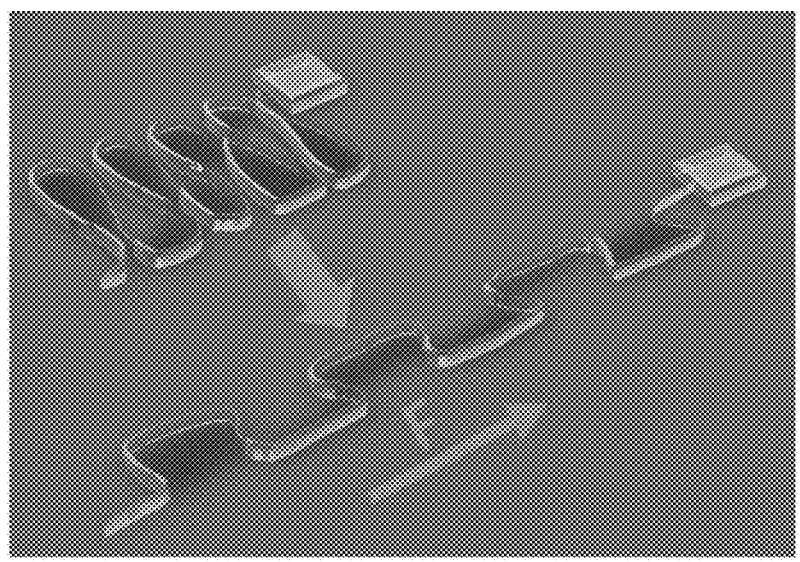

FIG. 20 presents a schematic illustration of an electronic element featuring a curled morphology which can be stretched, according to some embodiments of the present invention.

Figure 21:
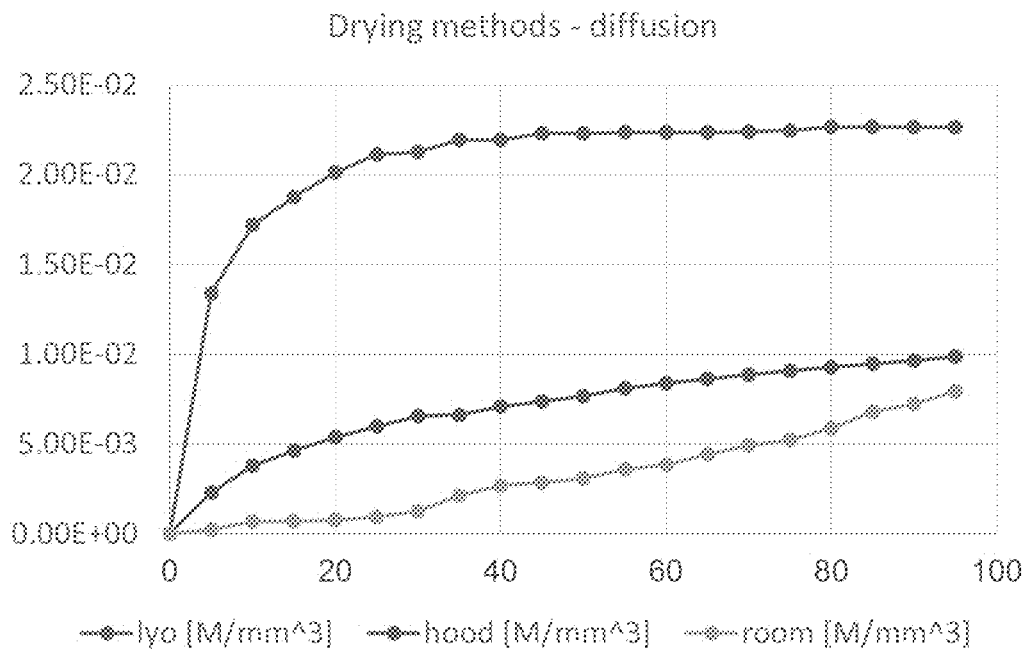

FIG. 21 presents comparative plots showing the effect of the drying method of the release profile of dopamine from a PolyAMPS-containing, hydrogel by diffusion.

Figure 22:
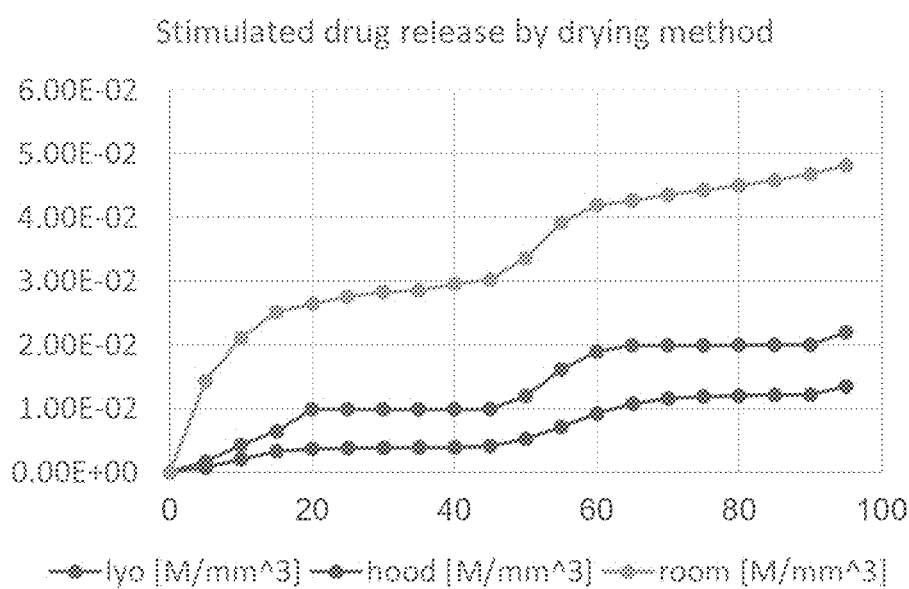

FIG. 22 presents comparative plots showing the effect of the drying method of the release profile of dopamine from the dried a PolyAMPS-containing hydrogel upon electric stimulation.

Figure 23:
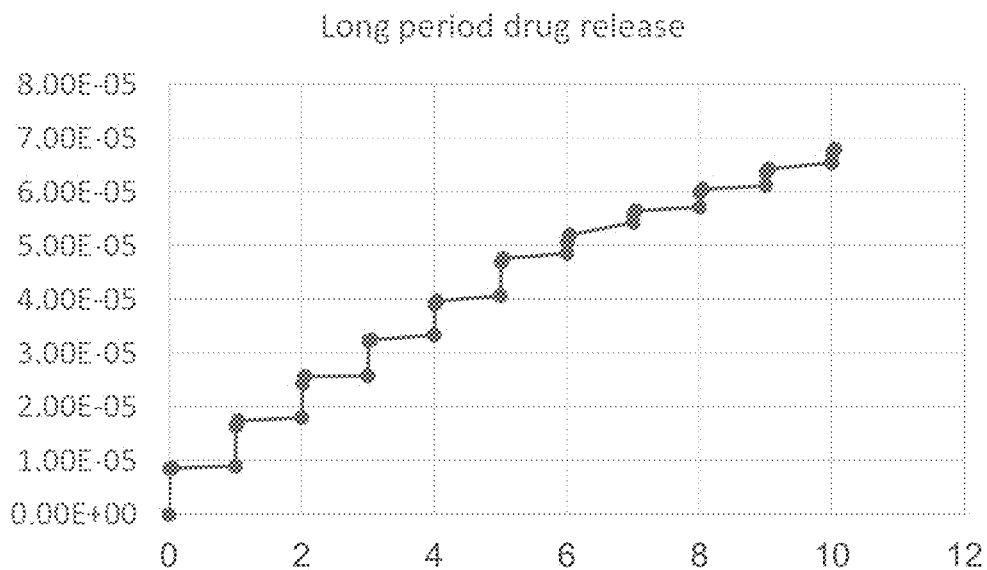

FIG. 23 presents a graph showing the long-term release profile of dopamine upon electric stimulation, from a PolyAMPS-containing hydrogel dried by lyophilization.

Figure 24:
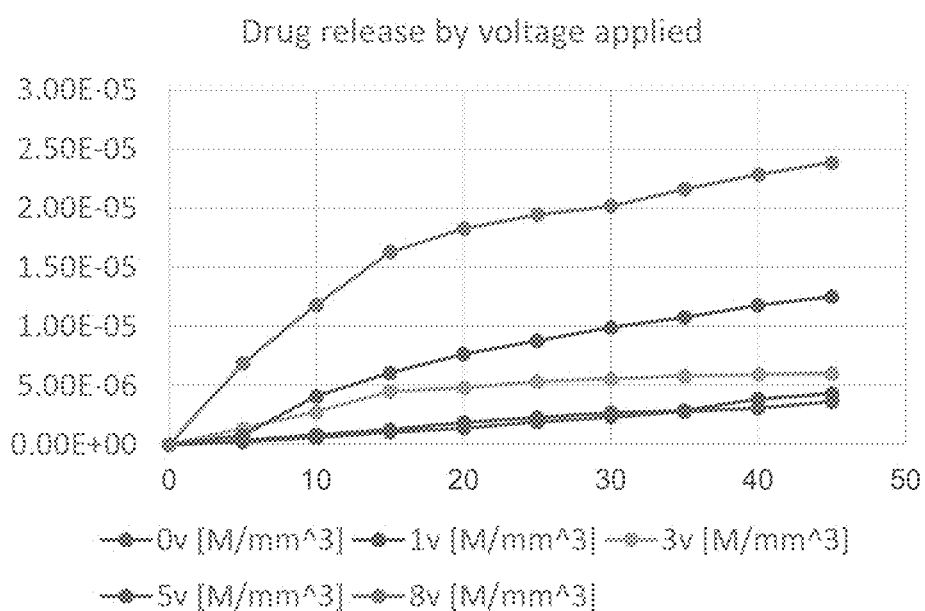

FIG. 24 presents comparative plots showing the release profile of dopamine from a PolyAMPS-containing hydrogel dried by lyophilization as a function of the applied potential.

Figure 25:
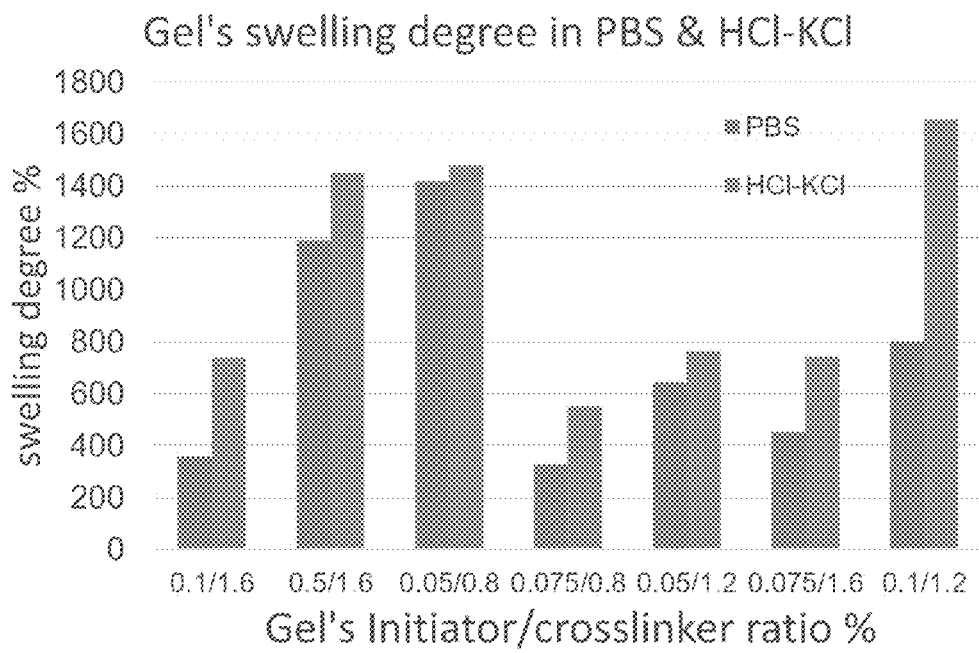

FIG. 25 presents a bar graph showing the swelling degree of a PolyAMPS-containing hydrogel as a function of the molar ratio of cross linker and initiator used during gel polymerization.

Figure 26:
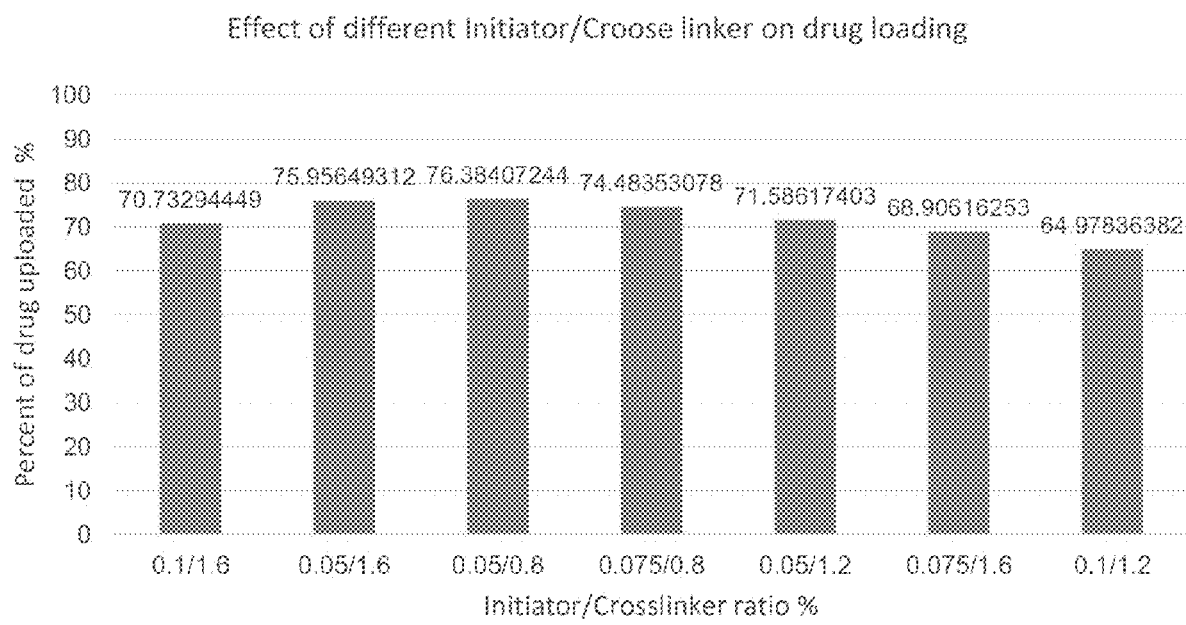

FIG. 26 presents a bar graph showing the amount of dopamine loaded into a PolyAMPS-containing hydrogel as a function of the initiator/cross-linking agent molar ration.

Figure 27:
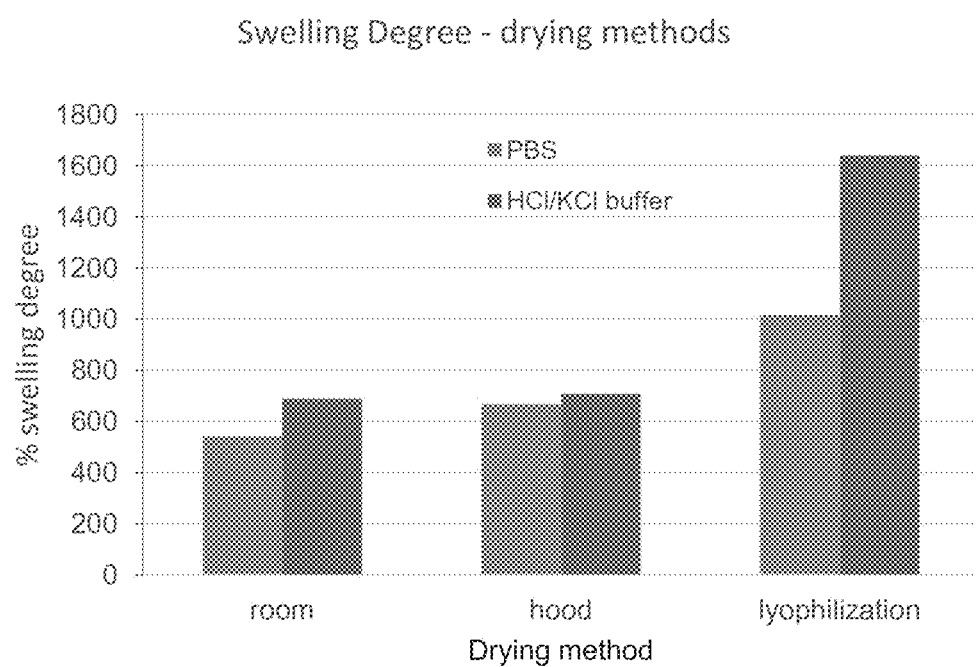

FIG. 27 presents a bar graph showing the effect of the drying method on the swelling capacity of a PolyAMPS-containing hydrogel.

Figure 28:
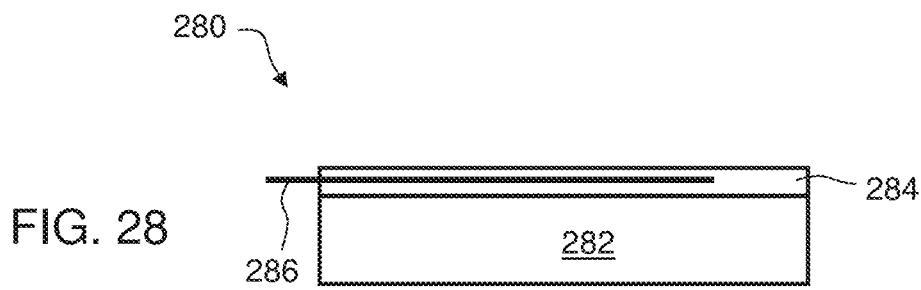

FIG. 28 is a schematic illustration of a scaffold device according to some embodiments of the present invention.

Figure 29A:
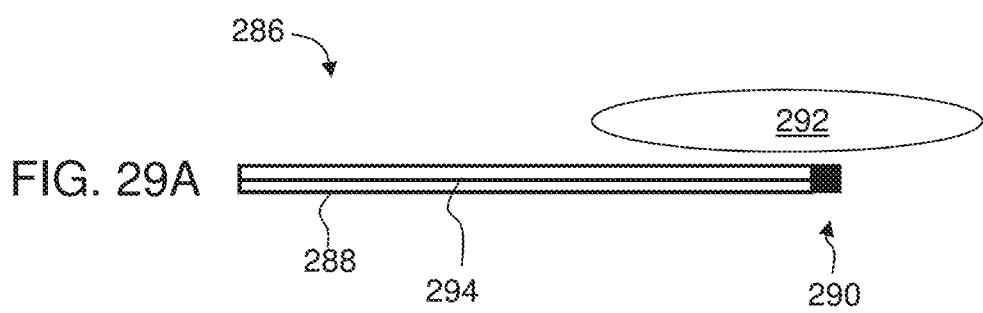
Figure 29B:
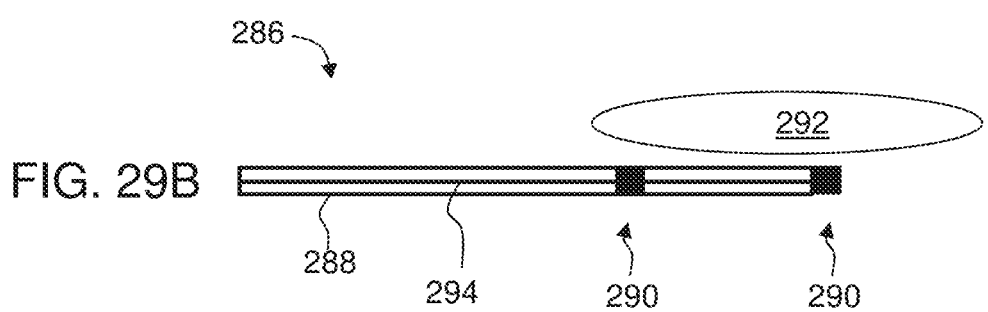

FIGS. 29A-B are schematic illustrations of an electrode according to some embodiments of the present invention.

Figure 30:
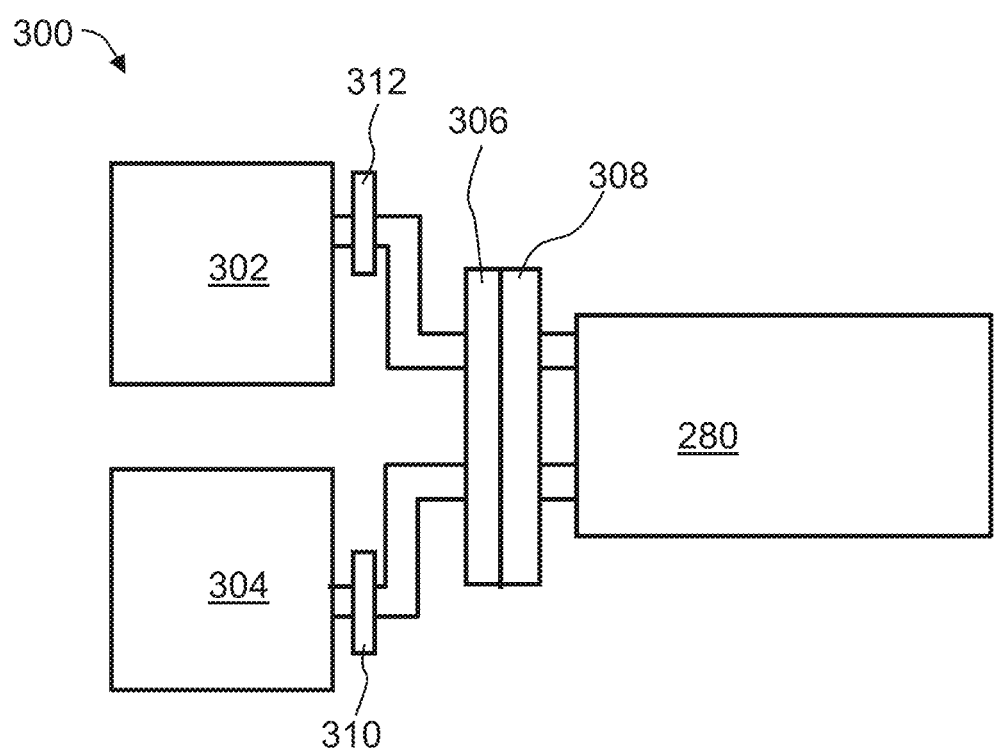

FIG. 30 is a schematic illustration of a system for controlling, treating and/or extracting information from cells and/or tissues incorporated in and/or on a scaffold element in a device according to some embodiments of the present invention.

DESCRIPTION OF SPECIFIC EMBODIMENTS OF THE INVENTION

The present invention, in some embodiments thereof, relates to tissue engineering and, more particularly, but not exclusively, to an electronic scaffold, engineered tissue made therefrom and uses thereof.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present inventors have devised and successfully prepared and practiced a scaffold device (herein also referred to as "an electronic scaffold") which can be used for establishing communication between an electronic circuit and a biological material. The scaffold device can be employed in many applications, including, without limitation, implantation in the body of a subject, e.g., a mammalian subject, for example, as an engineered tissue; monitoring and/or stimulation of an activity and/or a function of a cell (e.g., a tissue cell), either in vivo or in vitro; control release of an agent, e.g., a therapeutically active agent;

and/or screening of chemical or biological agents, so as, for example, determining a toxicity or efficacy of therapeutically active agents.

Herein throughout, a "biological material" is meant to include a cell, cells and/or a tissue.

In some embodiments of the present invention the scaffold device is used for tissue engineering. For example, the scaffold device can be used for engineering a cardiac patch, e.g., for the purpose of replacing a scar tissue formed on the heart after heart attack. The scaffold device can optionally and preferably facilitates pacing, monitoring and/or releasing drugs in the engineered tissue (e.g., cardiac patch).

The scaffold device can be used for measuring action potentials, e.g., in natural or engineered cardiac and neuronal tissues. The scaffold device can also serve as, or be a component of a pacemaker.

While some of the embodiments below are described with a particular emphasis to cardiac tissue, it is to be understood that more detailed reference to cardiac tissue is not to be interpreted as limiting, and that the present embodiments also contemplate use of the scaffold device for engineering, and/or monitoring and/or stimulating and/or treating other tissues such as, but not limited to, liver tissue. The scaffold device of the some embodiments can also be used for monitoring cell secretions, such as albumin.

In some embodiments, the scaffold device is used to make up a final product such as, for example, a cyborg tissue ready for implant into a patient. A patient can be, for example, one who has suffered from a myocardial infarction and needs to treat the necrotic tissue. The engineered (cyborg) tissue is implanted on the heart with a miniature wireless power source and monitored and controlled from outside. The scaffold device of the present embodiments can then be used, e.g., to monitor heart function, provide electrical support as a pacemaker, and/or release therapeutically active agents (e.g., drugs or factors) in a controlled manner.

The scaffold device optionally and preferably comprises an electronic element and a three-dimensional polymeric element associated therewith. The electronic element and the scaffold element can be integrated together, for example, by embedding the electronic element into the scaffold element, depositing the scaffold element on or around the electronic element, and/or be attached to each other, for example, in a layerwise manner.

In some embodiments, the electronic element serves for establishing communication between the electronic circuit and the scaffold element and/or cells or tissues associated with scaffold element, and the scaffold element serves for establishing communication between cells or tissues and the electronic element. The latter communication can be via a direct contact between the cells or tissue and the electronic element. Additionally or alternatively, the scaffold element or a portion thereof may be made conductive in which case at least some electrical signals can be transferred between the electronic element and cells or tissues associated with the scaffold element via electrical current flowing in the scaffold element.

In some embodiments, the electronic element serves for activating or deactivating certain functions possessed by the scaffold element, in which case the scaffold element is made electro-responsive. In these embodiments, the electronic element may or may not communicate with cells or tissue associated with the scaffold element.

Combination of the above embodiments is also contemplated in some embodiments. Thus, the present embodiments contemplate a device in which the electronic element serves both for establishing communication between the electronic circuit and cells and/or tissue associated with the scaffold element, and for activating or deactivating certain functions possessed by the scaffold element. In these embodiments, the scaffold element is both electro-responsive and serves for establishing communication between the cells or tissue associated with the scaffold element and the electronic element.

Representative examples of uses of the electronic element of the present embodiments, include, without limitation, (i) recording and/or monitoring a function and/or activity of a tissue, such as, but not limited to, cardiac tissue, for example, by characterizing propagation (e.g., propagation path, propagation speed, propagation velocity); (ii) stimulation of a tissue (e.g., an engineered tissue); (iii) releasing a therapeutically active agent (e.g., drugs and/or biomolecules) into a biological microenvironment (e.g., tissue, an engineered tissue), e.g., for improving tissue performance; (iv) on-line screening of therapeutically active agents (e.g., for determining agent's toxicity and/or efficacy).

Some embodiments of the present invention provide therapy for an infracted heart, and/or on-line monitoring and pacing of the heart. Furthermore the scaffold device of the present embodiments may be used for on-line screening of cardiotoxicity of drugs and for basic science experiments in cardiology.

Some exemplary embodiments of the invention pertain to a self-supporting flexible electronic element composed of a SU-8-based polymeric layer and a core made of gold, which can be integrated within a scaffold for tissue engineering. The scaffold device of the present embodiments allows a 3D confluent tissue assembly and allows internal control and monitoring of the tissue or cells forming the tissue.

In experiments performed by the present inventors, an exemplary scaffold device was made up of a mesh of SU-8 (an epoxy photoresist) and gold electrodes delicate enough to contact specific regions of the tissue down to single cell resolution. The electrodes were integrated within 3D polymeric fibrous scaffold elements (e.g., made up of nanofibers, microfibers or being macroporous). Cardiac cells were then seeded into the scaffold elements. After cardiac cell seeding, action potentials were simultaneously recorded from the scaffold device across multiple electrodes. Signal velocity across the tissue was then calculated based on the recorded action potentials.

In further experiments performed by the present inventors, electro-responsive hydrogels were deposited onto gold electrodes selectively coated with a thin SU-8 layer. Positive and negative electro-responsive hydrogels having oppositely-charged active agents attached thereto via electrostatic interactions, and the release profiles of these agents upon electrical stimulation, were also studied.

Referring now to the drawings, FIG. 28 is a schematic illustration of a scaffold according to some embodiments of the present invention. Device 280 optionally and preferably comprises a three-dimensional scaffold element 282 and an electronic element 284 being in contact with scaffold element 282. FIG. 28 shows element 284 attached to scaffold element 282 from above, but this need not necessarily be the case, since, for some applications, element 284 can be embedded in scaffold element 282 or attached to scaffold element 282 from below.

Scaffold element 282 is optionally and preferably made of a polymeric material, as defined and described hereinafter. Representative examples of polymeric material suitable for the present embodiments are provided hereinunder.

An exemplary scaffold device according to some embodiments of the present invention is also presented in FIG. 1B.

The Electronic Element:

Electronic element 284 preferably comprises one or more electrode 286 which can be connected to a measuring device (not shown in FIGS. 1A-B) and/or a controller (not shown). For clarity of presentation, FIG. 28 shows a single electrode, but one of ordinary skills in the art, provided with the details described herein would know how to construct an electronic element with a plurality of electrodes. When element 284 comprises a plurality of electrodes, each electrode is optionally and preferably individually connected to the measuring device and/or controller, so as to form independent communication channels between the scaffold device 280 and the measuring device and/or controller. In some of any of the embodiments described herein, the electrodes 286 form a mesh, and in some embodiments of the invention the electrodes within the element are parallel to one another.

In some embodiments, the electrode(s) are connected to the polymeric element such that the electrode(s) externally engage cells present at the site at which the device is implanted. In these embodiments, the electrode(s) serves as an extracellular electrode, and the voltage sensitivity of the electrode(s) is preferably selected to allow sensing extracellular potentials. Typically, the voltage sensitivity of the electrode structures may vary from 1 microvolt to 1 volt.

Generally, each electrode has a conductive core and an electrically-isolating layer.

The conductive core can be made of an electrically-conducting material such as for example, gold (Au) or any other conductive metals, or any combination thereof, as described herein. Preferably, the core is made of a biocompatible material. An example includes a combination of gold (Au) and chromium (Cr), with gold being 50 weight percents or more, preferably 60, 70, 80 weight percents or more, and even 100% gold. Other electrically-conducting materials are contemplated, including, but not limited to, Al, Ti, Ni, Ag, Cr, Pd, Mo, Nb, Cu, Pt, Ag, and Co.

In some embodiments, the conductive core further comprises an additional layer of electrically-conductive material, preferably a biocompatible material. In some embodiments, the additional layer is such that imparts to the electrode, optionally at selected areas, roughness.

The electrically-isolating layer is made of a substance that is non-conductive under application of voltage. In some embodiments, the electrically-isolating layer is a polymeric layer, made of electrically-insulating polymers, preferably biocompatible such polymers, and optionally and preferably curable polymers, which, upon curing, may provide the electrode(s) with a desired strength or flexibility or elasticity. Examples include, without limitation, epoxy resins, preferably epoxy photoresists, for example a SU-8 photoresist, polyimides, and silica-based polymers (e.g., PDMS). Other electrically-isolating polymeric materials and materials in general are also contemplated.

A SU-8 photoresist is near UV photoresist based on a SU-8 epoxy resin, as described, for example, in U.S. Pat. Nos. 4,237,216 and 4,882,245. Any photoresist of the SU-8 family is contemplated herein.

Exemplary polyimides usable for forming the polymeric layer include, without limitation, polymers of the family of photosensitive polyimides (PSPI).

A schematic illustration of electrode 286 is shown in FIGS. 29A-B. Electrode 286 has a conductive core 294 and an electrically-isolating layer 288 deposited on core 294 such that a portion 290 of electrode 286 remains partially uncoated in a predetermined of scaffold element 282 location and consequently exposed to an environment 292 surrounding electrode 286. Environment 292 can be the 3D polymeric material of the scaffold element 282 and/or cells or tissue grown within the 3D polymeric material, or can be a physiological environment, for example, cells or a tissue of an organ which are engaged with an implanted scaffold device.

Core 294 can be made of an electrically-conducting material such as for example, gold (Au) or any other conductive metals, or any combination thereof, as described herein. Layer 288 can be made, for example, from a non-conductive polymeric material. Preferably, layer 288 is a polymeric layer, as described herein. The thickness of layer 288 can range from about 0.1 micron to about 100 microns, or from 1 micron to about 100 microns, or from about 1 micron to about 50 microns, or from about 10 microns to about 30 microns, including any intermediate subranges and values. The thickness of layer 288 is preferably selected to maintain predetermined mechanical properties such as strength, elasticity and flexibility.

Portion 290 can have a dimension of from 1 to 100 microns, preferably from 1 to 50 microns, or from 10 to 50 microns, including any subranges and values therebetween.

In some embodiments of the present invention electrode 286 is exposed to environment 292 at a tip of electrode 286 (FIG. 29A), and in some embodiments of the present invention electrode 286 is exposed to environment 292 at a plurality of discrete locations over electrode 286 (FIG. 29B).

Electrode 286 can be a microelectrode, such that at least one dimension of the electrode ranges from 1 micron to 2000 microns or from 1 micron to 1000 microns. The size of the electrode can be determined according to its intended use, and can be defined by varying parameters of the process of preparing the electrode structure.

Electrode 286 is preferably flexible and can have any shape. In some embodiments, electrode 286 is disposed on, below or within scaffold element 282 along a generally straight line. In some embodiments electrode 286 is disposed on, below or within scaffold element 282 along a curved line, which can be planar or non-planar. Representative examples of shapes of curved lines suitable for the present embodiments include, without limitation, a wavy line (e.g., a zigzag line, a sinusoidal line, a square wave line, a saw-tooth line), a curvilinear line, a spiral line, a serpentine line, a cycloid, a helical line and any combination thereof.

The advantage of having an electrode shape describing a curved line is that it allows the electrode to adapt to geometrical changes in the scaffold element. For example, when the scaffold element bends of folds, the curved electrode can stretch so as to conform to the new shape of the scaffold element. The present inventors demonstrated re-shaping electrodes while maintaining a generally constant (e.g., with a tolerance of less than 10% or less than 5% or less than 2%) conductivity as a function of the strain of the electrode.

The Scaffold Element:

Herein, a scaffold describes a three-dimensional open lattice matrix, typically in a form of a network of microfibers or nanofiber, or in a form of a microporous network.

The scaffold's structure allows entrapment or loading of substances such as water, small molecules and biomolecules, including cells and tissues.

In some embodiments, the scaffold is a matrix that allows cells to be cultured (i.e., survive and preferably proliferate) thereon and/or therewithin.

A scaffold element as described herein is made of a polymeric material, and is also referred to herein throughout, interchangeably as a three-dimensional polymeric element.

By "polymeric material" it is meant a single polymer or co-polymer, or two or more of polymers and/or co-polymers. There are no particular limitations to the number or arrangement of polymers used in forming the scaffold as described herein.

The composition of the polymeric material, namely, the polymer or co-polymer or the ratio of different polymers and/or co-polymers in a mixture of choice, determines mechanical, physical, chemical and biological properties of the scaffold.

For example, the molecular weight and cross-link density of the polymeric material may be selected to control both the mechanical properties of the scaffold and the degradation rate (for degradable scaffolds). The polymeric material of choice determines the degradability or biodegradability of the scaffold. The electrical properties of the polymeric material determine its performance when subjected to electric stimuli.

A polymeric material composing the scaffold may comprise natural and/or synthetic polymers or co-polymers. In some embodiments, the polymeric material comprises biocompatible polymer and/or co-polymer. In some embodiments, the polymeric material, and the scaffold made therefrom is biodegradable and/or bioerodible, yet non-resorbing or non-biodegradable polymeric materials are also contemplated.

The phrase "non-biodegradable polymer", as used herein, describes a substance which does not undergo degradation under physiological and/or environmental conditions. This term typically refers to substances which decompose under these conditions such that more than 50 percents do not decompose within at least 1 year, preferably within 2 years, 3 years, 4 years, and up to 10 years and even 20 or 50 years.

The terms "non-biodegradable" and "non-resorbing" are equivalent and are used interchangeably herein.

Such non-resorbing polymeric materials may be used to fabricate scaffold structures which are designed for long term or permanent implantation into a host organism.

In exemplary embodiments, non-biodegradable polymeric materials may be biocompatible. Examples of biocompatible non-biodegradable polymeric materials which are useful as scaffold materials include, but are not limited to, polyethylenes, polyvinyl chlorides, polyamides such as nylons, polyesters, rayons, polypropylenes, polyacrylonitriles, acrylics, polyisoprenes, polybutadienes and polybutadiene-polyisoprene copolymers, neoprenes and nitrile rubbers, polyisobutylenes, olefinic rubbers such as ethylene-propylene rubbers, ethylene-propylene-diene monomer rubbers, and polyurethane elastomers, silicone rubbers, fluoroelastomers and fluorosilicone rubbers, homopolymers and copolymers of vinyl acetates such as ethylene vinyl acetate copolymer, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyvinylpyrrolidones, polyacrylonitrile butadienes, polycarbonates, polyamides, fluoropolymers such as polytetrafluoroethylene and polyvinyl fluoride, polystyrenes, homopolymers and copolymers of styrene acrylonitrile, cellulose acetates, homopolymers and copolymers of acrylonitrile butadiene styrene, polymethylpentenes, polysulfones, polyesters, polyimides, polyisobutylenes, polymethylstyrenes, and other similar compounds known to those skilled in the art.

In other embodiments, the structural scaffold materials may be a "bioerodible" or "biodegradable" polymer or co-polymer or combinations thereof.

The term "biodegradable" as used in the context of the present invention, describes a material which can decompose under physiological and/or environmental conditions into breakdown products. Such physiological and/or environmental conditions include, for example, hydrolysis (decomposition via hydrolytic cleavage), enzymatic catalysis (enzymatic degradation), and mechanical interactions. This term typically refers to substances that decompose under these conditions such that 50 weight percents of the substance decompose within a time period shorter than one year.

The term "biodegradable" as used in the context of the present invention, also encompasses the term "bioresorbable", which describes a substance that decomposes under physiological conditions to break down to products that undergo bioresorption into the host-organism, namely, become metabolites of the biochemical systems of the host-organism.

The terms "biodegradable" and "bioerodible" and "bioresorbable" are equivalent and are used interchangeably herein.

Such bioerodible or biodegradable polymeric materials may be used to fabricate temporary scaffold structures.

In exemplary embodiments, biodegradable or bioerodible structural scaffold materials may be biocompatible. Examples of biocompatible biodegradable polymers which are useful as scaffold materials include, but are not limited to, polylactic acid, polyglycolic acid, polycaprolactone, and copolymers thereof, polyesters such as polyglycolides, polyanhydrides, polyacrylates, polyalkyl cyanoacrylates such as n-butyl cyanoacrylate and isopropyl cyanoacrylate, polyacrylamides, polyorthoesters, polyphosphazenes, polypeptides, polyurethanes, polystyrenes, polystyrene sulfonic acid, polystyrene carboxylic acid, polyalkylene oxides, alginates, agaroses, dextrins, dextrans, polyanhydrides, biopolymers such as collagens and elastin, alginates, chitosans, glycosaminoglycans, and co-polymers made of any mixture of such polymers and mixtures of such polymers or co-polymers.

In still other embodiments, a mixture of non-biodegradable and bioerodible and/or biodegradable polymeric materials may be used to form a biomimetic scaffold structure of which part is permanent and part is temporary.

In some embodiments, the scaffold is made of a polymeric material that is suitable for cell growth and/or for cell adherence. In some embodiments, the scaffold is made of a polymeric material that provides favorable conditions for cells to adhere, proliferate, and organize into a form of a tissue.

Representative examples such polymeric materials include, but are not limited to, polycaprolactone (PCL), gelatin, poly(lactic acid (PLA), poly(glycolic acid) (PGA), poly(lactic acid-co-glycolic acid) (PLGA), albumin, alginate, decellularized extracellular matrix, as described herein and a variety of other hydrogels, polymers and other materials, and any combination thereof.

In an exemplary embodiment, the polymeric material comprises PCL, gelatin or a combination of PCL and gelatin.

In further exemplary embodiments, the polymeric material comprises naturally occurring substances, such as, fibrinogen, fibrin, thrombin, chitosan, collagen, alginate, poly(N-isopropylacrylamide), hyaluronate, albumin, collagen, synthetic polyamino acids, prolamines, polysaccharides such as alginate, heparin, and other naturally occurring biodegradable polymers of sugar units.

In an exemplary embodiment, the polymeric material comprises albumin.

In some of these embodiments, the scaffold element is made of or comprises a fibrous polymeric material, and in some embodiments, the fibrous polymeric material comprises nanofibers of the polymer. Fibrous polymeric material can be obtained, for example, by electrospinning, as described in detail hereinunder.

Thus, in some of these embodiments, the scaffold element comprises an electrospun, or otherwise formed, fibrous polymeric material, for example, an electrospun or otherwise formed, fibrous polycaprolactone (PCL), gelatin, poly (lactic acid (PLA), poly(glycolic acid) (PGA), poly(lactic acid-co-glycolic acid) (PLGA), albumin, and/or alginate.

In further exemplary embodiments, the polymeric material comprises one or more electro-responsive polymer or co-polymer.

The phrase "electro-responsive polymer", which is also referred to herein and in the art, interchangeably, as "electroactive polymer", describes a polymer or co-polymer which undergoes a change in its shape, structure and/or chemical properties in response to electric stimuli.

In some embodiments, the electro-responsive polymer undergoes a change in its chemical structure such that upon application of voltage, a change in its electronic structure occurs. In some embodiments, the change in the electronic structure is exhibited as a change in the net charge of the polymer, and, in some embodiments, this change is reflected by a change in the net charge of at least some of the functional groups of the polymer.

Electro-responsive polymers can be, for example, polymers or co-polymers having positively-charged groups (either pendant groups or backbone groups), which, upon potential application, are converted into neutral groups. Exemplary such polymers include, for example, polyporrole, poly(vinyl amines), poly(vinyl pyridine), and poly (vinyl imidazole).

Electro-responsive polymers can be, for example, polymers or co-polymers having negatively-charged groups (either pendant groups or backbone groups), which, upon potential application, are converted into neutral groups. Exemplary such polymers include, but are not limited to, ionic polysaccharides, such as alginates or chitosan, poly (phosphazenes), poly(acrylic acids), and poly(methacrylic acids), and other polymers having negatively-charged groups (either pendant groups or backbone groups) such as carboxylic acid groups, sulfonic acid groups, and halogenated (preferably fluorinated) alcohol groups.

One example is poly(acrylamide-2-methylpropanesulfonic acid) or a co-polymer comprising same.

By "pendant groups" it is meant herein, and in the art, groups within the side chains of the polymer's backbone units. For example, a pyridine group is a poly(vinylpyridine) is a positively charged pendant group.

By "backbone groups" it is meant herein, and in the art, groups within the polymer's backbone units, which form the polymeric backbone. For example, the nitrogen atom of a pyrrole backbone unit of a polypyrrole is a positively-charged backbone group.

By "positively-charged" and "negatively-charged", it is meant a net charge in a physiological environment, for example, an aqueous solution at pH of about 7.

In some embodiments, the three-dimensional polymeric element is in a form of a hydrogel. The hydrogel may be a lyophilized or otherwise dried hydrogel.

In some embodiments, the hydrogel is made of an electro-responsive polymer, as described herein. Electro-responsive polymers can be prepared, for example, by chemical polymerization (e.g., radical polymerization) or by electropolymerization.

According to still another embodiment, the scaffold is generated from decellularized tissue and more specifically from decellularized extracellular matrix (ECM) of a tissue.

As used herein the phrase "decellularized ECM of a tissue" refers to the extracellular matrix which supports tissue organization (e.g., a natural tissue) and underwent a decellularization process (i.e., a removal of all cells from the tissue) and is thus completely devoid of any cellular components.

The phrase "completely devoid of any cellular components" as used herein refers to being more than 90%, 91%, 92%, 93%, 94%, 95%, 96%, 97%, 98%, 99%, (e.g., 100%) devoid of the cellular components present in the natural (e.g., native) tissue. As used herein, the phrase "cellular components" refers to cell membrane components or intracellular components which make up the cell. Examples of cell components include cell structures (e.g., organelles) or molecules comprised in same. Examples of such include, but are not limited to, cell nuclei, nucleic acids, residual nucleic acids (e.g., fragmented nucleic acid sequences), cell membranes and/or residual cell membranes (e.g., fragmented membranes) which are present in cells of the tissue. It will be appreciated that due to the removal of all cellular components from the tissue, such a decellularized matrix cannot induce an immunological response when implanted in a subject.

The phrase "extracellular matrix (ECM)" as used herein, refers to a complex network of materials produced and secreted by the cells of the tissue into the surrounding extracellular space and/or medium and which typically together with the cells of the tissue impart the tissue its mechanical and structural properties. Generally, the ECM includes fibrous elements (particularly collagen, elastin, or reticulin), cell adhesion polypeptides (e.g., fibronectin, laminin and adhesive glycoproteins), and space-filling molecules [usually glycosaminoglycans (GAG), proteoglycans].

A tissue-of-interest (e.g., pancreas, myocardium, omentum) may be derived from an autologous or non-autologous tissue (e.g., allogeneic or even xenogeneic tissue, due to non-immunogenicity of the resultant decellularized matrix). The tissue is removed from the subject [e.g., an animal, preferably a mammal, such as a pig, monkey or chimpanzee, or alternatively, a deceased human being (shortly after death)] and can be washed e.g. in a sterile saline solution (0.9% NaCl, pH=7.4) or phosphate buffered saline (PBS), which can be supplemented with antibiotics such as Penicillin/Streptomycin 250 units/ml. Although whole tissues can be used, for several applications segments of tissues may be cut e.g. sliced. Such tissue segments can be of various dimensions, depending on the original tissue used and the desired application.

Methods of decellularizing tissue are known in the art. See, for example, U.S. Patent Application Publication Nos. 20120156250, 20050013870 and 201000267143, PCT Application Publication Nos. WO 2014/037942 and WO 2009/085547, and U.S. Patent Application No. 61/838,428.

Typically, the scaffold elements of the present embodiments feature a porous structure. The porosity of the scaffold may be controlled by a variety of techniques known to those skilled in the art. The minimum pore size and degree of porosity is dictated, for example, by the need to provide enough room for the cells and for nutrients to filter through the scaffold to the cells, or by the need to releasably incorporate therapeutically active agents, as described hereinafter.

The maximum pore size and porosity is limited by the ability of the scaffold to maintain its mechanical stability. As the porosity is increased, use of polymers having a higher modulus, addition of stiffer polymers as a co-polymer or mixture, or an increase in the cross-link density of the polymer may all be used to increase the stability of the scaffold.

The scaffold elements described herein may be made by any of a variety of techniques known to those skilled in the art. Salt-leaching, porogens, solid-liquid phase separation (sometimes termed freeze-drying or lyophilization), and phase inversion fabrication may all be used to produce porous scaffolds. Fiber pulling and weaving (see, e.g. Vacanti, et al., (1988) Journal of Pediatric Surgery, 23: 3-9) may be used to produce scaffolds having more aligned polymer threads. Those skilled in the art will recognize that standard polymer processing techniques may be exploited to create polymer scaffolds having a variety of porosities and microstructures.

The scaffold element can be generated separately and then be constructed so as to be in contact with the electronic element, or be fabricated directly in the presence of the electronic element.

According to a particular embodiment, the scaffold is made by electrospinning the polymeric material, that is, it comprises an electrospun polymeric material.

In some of these embodiments, the electrospinning is performed in the presence of the electronic component, as is exemplified in the Examples section the follows.

As used herein, the term "electrospinning" refers to a technology which produces electrospun fibers (e.g. nanofibers) from a polymer solution. During this process, one or more polymers of the polymeric material as described herein are liquefied (i.e. melted or dissolved) and placed in a dispenser. An electrostatic field is employed to generate a positively charged jet from the dispenser to the collector. Thus, a dispenser (e.g., a syringe with metallic needle) is typically connected to a source of high voltage, preferably of positive polarity, while the collector is grounded, thus forming an electrostatic field between the dispenser and the collector. Alternatively, the dispenser can be grounded while the collector is connected to a source of high voltage, preferably with negative polarity. As will be appreciated by one ordinarily skilled in the art, any of the above configurations establishes motion of positively charged jet from the dispenser to the collector. Reverse polarity for establishing motions of a negatively charged jet from the dispenser to the collector is also contemplated. At the critical voltage, the charge repulsion begins to overcome the surface tension of the liquid drop. The charged jets depart from the dispenser and travel within the electrostatic field towards the collector. Moving with high velocity in the inter-electrode space, the jet stretches and the solvent therein evaporates, thus forming fibers which are collected on the collector forming the electrospun scaffold.

Several parameters may affect the diameter of the fiber, these include, the size of the dispensing hole of the dispenser, the dispensing rate, the strength of the electrostatic field, the distance between the dispenser and/or the concentration of the polymeric material used for fabricating the electrospun fiber.

According to some embodiments, the average fiber diameter is between 20 nm-10 μm, 20 am-1 μm, 100-300 nm, e.g. about 250 nm.

The dispenser can be, for example, a syringe with a metal needle or a bath provided with one or more capillary apertures from which the liquefied polymeric material as described herein can be extruded, e.g., under the action of hydrostatic pressure, mechanical pressure, air pressure and high voltage.

According to one embodiment, the collector is a rotating collector which serves for collecting the electrospun scaffold thereupon. Employing a rotating collector can result in an electrospun scaffold with a continuous gradient of porosity. Such a porosity gradient can be achieved by continuous variation in the velocity of the collector or by a longitudinal motion of the dispenser, these result in a substantial variation in the density and/or spatial distribution of the fibers on the collector and thus, result in a porosity gradient along the radial direction or along the longitudinal direction of the collector, respectively. Typically, but not obligatorily, the rotating collector has a cylindrical shape (e.g., a drum), however, it will be appreciated that the rotating collector can be also of a planar geometry.

According to another embodiment, the collector is a flat ground collector which serves for collecting the electrospun scaffold thereupon. Employing a flat ground collector enables collection of random nanofibers. It will be appreciated that the flat ground collector is typically a horizontal collector or a vertical collector.

According to another exemplary embodiment, adhesive agents are included in the scaffolds (e.g. electrospun fibrous polymeric material) of some of the present embodiments. Such adhesive agents may be used to unite or bond the electrospun polymers together.

Such an adhesive agent may include, without being limited to, gelatin, fibrin, fibronectin, collagen or RGB. Ratios of adhesive agents (e.g. gelatin): polymer may be about 50:50, may be about 40:60, may be about 30:70, may be about 20:80, or may be about 10:90.

According to a particular embodiment, the scaffold comprises spring-like fibers (i.e. coiled fibers), that are also able to stretch with extensibility over 200%, and recoil back to the same position. Such fibers can be generated by electrospinning by fixing the rate of delivery of the polymer solution through the capillary. Thus, for example, the present inventors have shown that spring-like fibers can be generated if a polymer solution of PCL (e.g. at concentrations between 10% to 17.5% w/v %) dissolved in dichloromethane (DCM) and dimethylformamide (DMF) (for examples in ratios of 3:1, 2:1, 1:1 and 1:2) through a capillary at a rate of 0.1-20 ml/h (e.g. 0.5 ml/h).

Spring-like fibers can also be generated using PLGA.

Table 1 below presents exemplary compositions which are usable for forming electrospun polymeric material as a scaffold element as described herein.

TABLE 1

| Materials | Solvent |
|---|---|
| Natural polymers | |
| Chitosan | 90% Acetic acid |
| Gelatin | Formic acid |
| Gelatin | TFE |
| Collagen Type I, II, and III | HFIP |
| Collagen Type I, II, and III | HFIP |
| Collagen Type I, II, and III | HFIP |
| Elastin | HFIP |
| Hyaluronic acid | DMF/water |
| Cellulose | NMMO/water |
| Silk fibroin | Methanol |

TABLE 1-continued

| Materials | Solvent |
|---|---|
| Phospholipids (Lecithin) | Chloroform/DMF |
| Fibrinogen | HFIP/10 × minimal essential medium |
| Hemoglobin | TFE |
| Fibrous calf thymus Na-DNA | Water/ethanol |
| Virus M13 viruses | THF |
| Synthetic polymers | |
| PLGA | TFE/DMF |
| PLA | HFIP |
| PLA | DCM |
| PLA | DCM/DMF |
| PLA | DCM/pyridine |
| PCL | DCM/methanol |
| PHBV | Chloroform/DMF |
| PDO | HFIP |
| PGA | HFIP |
| PLCL | Acetone |
| PLCL | DCM |
| PLLA-DLA | Chloroform |
| PEUU | HFIP |
| Cellulose acetate | Acetic acid/water |
| PEG-b-PLA | Chloroform |
| EVOH | 70% propan-2-ol/water |
| PVA | Water |
| PEO | Water |
| PVP | Ethanol/water |
| Blended | |
| PLA/PCL | Chloroform |
| Gelatin/PVA | Formic acid |
| PCL/collagen | HFIP |
| Sodium aliginate/PEO | Water |
| Chitosan/PEO | Acetic acid/DMSO |
| Chitosan/PVA | Acetic acid |
| Gelatin/elastin/PLGA | HFIP |
| Silk/PEO | Water |
| Silk fibroin/chitosan | Formic acid |
| PDO/elastin | HFIP |
| PHBV/collagen | HFIP |
| Hyaluronic acid/gelatin | DMF/water |
| Collagen/chondroitin sulfate | TFE/water |
| Collagen/chitosan | HFIP/TFA |
| Composites | |
| PDLA/HA | Chloroform |
| PCL/CaCO$_3$ | Chloroform/methanol |
| PCL/CaCO$_3$ | DCM/DMF |
| PCL/HA | DCM/DMF |
| PLLA/HA | Chloroform |
| Gelatin/HA | HFIP |
| PCL/collagen/HA | HFIP |
| Collagen/HA | HFIP |
| Gelatin/siloxane | Acetic acid/ethyl acetate/water |
| PLLA/MWNTs/HA | 1, 4-dioxane/DCM |
| PLGA/HA | DCM/water |

Alternatively or additionally, the scaffold element as described herein is made of a polymeric material as described herein, which forms a hydrogel in contact with the electronic component as described herein.

In some of these embodiments, a hydrogel is formed directly in the presence of an electronic element as described herein. In exemplary embodiments, a hydrogel is made of an electropolymerizable monomer, which undergoes electropolymerization in the presence of the electronic element, which serves as the working electrode in the electropolymerization process.

In some of these embodiments, the hydrogel is formed separately, optionally dried, and thereafter the electronic element is integrated therewith.

According to some exemplary embodiments of the present invention, a combination of two or more of a hydrogel, a fibrous electrospun polymeric material and a decellularized matrix are used for forming the scaffold element as described herein. In some embodiments, the scaffold element comprises a hydrogel (e.g., dried hydrogel) made of an electro-responsive polymer and a fibrous polymeric material (e.g., electrospun polymeric material). In some of these embodiments, the fibrous polymeric material is deposited into the hydrogel.

The scaffolding can be varied by using a variety of different biopolymers, synthetic polymers, decellularized tissue scaffolds, macroporous scaffolds and more. These in turn, can also be altered to possess unique properties such as drug loading, different mechanical or electrical properties, and all the techniques used for tissue engineering.

Agents Incorporated in or on the Scaffold Element:

According to some of any of the embodiments of the present invention the device further comprises cells incorporated in the 3D polymeric element. Optionally and preferably, the cells form a tissue, such that the device represents an artificial tissue, also referred to herein as a cyborg tissue, or an engineered tissue.

In some of these embodiments, the scaffold element comprises 3D polymeric element comprised of a polymeric material that favors tissue formation, as described herein.

The cells can be, for example, endocardial cells, cardiac adrenergic cells, cardiac fibroblasts, vascular endothelial cells, smooth muscle cells, cardiac progenitor cells, adult stem cells, embryonic stem cells, mesenchymal stem cells, and any combination thereof.

The cells can be mammalian cells, including neonatal cells, adult or aged cells, progenitor cells (e.g., derived from a tissue selected from the group consisting of bone marrow, fat and umbilical cord), adult stem cells, embryonic stem cells, mesenchymal stem cells, genetically transformed cells and/or human cells.

Exemplary mammalian cells include but are not limited to cardiomyocytes, endocardial cells, cardiac adrenergic cells, cardiac fibroblasts, vascular endothelial cells, smooth muscle cells, cardiac progenitor cells, adult stem cells, embryonic stem cells, mesenchymal stem cells, and any combination thereof.

Any other cells are also contemplated.

The present embodiments envisage seeding any cells onto and/or within the scaffold. Preferably, the cells are viable and remain viable following the seeding. The cells may comprise a heterogeneous population of cells or alternatively the cells may comprise a homogeneous population of cells. Such cells can be for example, stem cells (such as embryonic stem cells, bone marrow stem cells, cord blood cells, mesenchymal stem cells, adult tissue stem cells), progenitor cells (e.g. progenitor bone cells), or differentiated cells such as chondrocytes, osteoblasts, connective tissue cells (e.g., fibrocytes, fibroblasts and adipose cells), endothelial and epithelial cells. Furthermore, the cells may be of autologous origin or non-autologous origin, such as postpartum-derived cells (as described in U.S. application Ser. Nos. 10/887,012 and 10/887,446). Typically the cells are selected according to the tissue being generated.

According to a particular embodiment, the cells comprise electrically excitable cells such as cardiac cell (e.g. cardiomyocyte), glandular cells and nerve cells (neurons).

As used herein, the term "cardiomyocytes" refers to fully or at least partially differentiated cardiomyocytes. Thus, cardiomyocytes may be derived from stem cells (such as embryonic stem cells or adult stem cells, such as mesenchymal stem cells). Methods of differentiating stem cells along a cardiac lineage are well known in the art [See, for example, Muller-Ehmsen J, et al., Circulation. 2002; 105: 1720-6; Zhang M, et al., J Mol Cell Cardiol. 2001; 33:907-

21, Xu et al, Circ Res. 2002; 91:501-508, and U.S. Pat. Appl. No. 20050037489, the contents of which are incorporated by reference herein]. According to one embodiment the stem cells are derived from human stem cell lines, such as H9.2 (Amit, M. et al., 2000. Dev Biol. 227:271).

Screening of partially differentiated cardiomyocytes may be performed by a method enabling detection of at least one characteristic associated with a cardiac phenotype, as described hereinbelow, for example via detection of cardiac specific mechanical contraction, detection of cardiac specific structures, detection of cardiac specific proteins, detection of cardiac specific RNAs, detection of cardiac specific electrical activity, and detection of cardiac specific changes in the intracellular concentration of a physiological ion.

Additional cells that may be seeded together with cardiomyocytes include for example endothelial cells and/or fibroblast cells (which may or may not be derived from cardiac tissue). Accordingly, a pool of cardiomyocytes, endothelial cells and fibroblasts (in the presence or absence of an appropriate gel, as described herein below) may be generated and seeded onto the scaffold.

Seeding of the cells on the scaffold element is an important step in the establishment of an engineered tissue. Since it has been observed that the initial distribution of cells within the scaffold after seeding is related to the cell densities subsequently achieved, methods of cell seeding require careful consideration. Thus, cells can be seeded in a scaffold by static loading, or by seeding in stirred flask bioreactors (scaffold is typically suspended from a solid support), in a rotating wall vessel, or using direct perfusion of the cells in medium in a bioreactor. Highest cell density throughout the scaffold is achieved by the latter (direct perfusion) technique.

The cells may be seeded directly onto the scaffold, or alternatively, the cells may be mixed with a gel which is then absorbed onto the interior and exterior surfaces of the scaffold and which may fill some of the pores of the scaffold. Capillary forces will retain the gel on the scaffold before hardening, or the gel may be allowed to harden on the scaffold to become more self-supporting. Alternatively, the cells may be combined with a cell support substrate in the form of a gel optionally including extracellular matrix components. An exemplary gel is Matrigel™, from Becton-Dickinson. Alternatively, the gel may be growth-factor reduced Matrigel, produced by removing most of the growth factors from the gel (see Taub, et al., Proc. Natl. Acad. Sci. USA (1990); 87 (10:4002-6). In another embodiment, the gel may be a collagen I gel, alginate, or agar. Such a gel may also include other extracellular matrix components, such as glycosaminoglycans, fibrin, fibronectin, proteoglycans, and glycoproteins. The gel may also include basement membrane components such as collagen IV and laminin. Enzymes such as proteinases and collagenases may be added to the gel, as may cell response modifiers such as growth factors and chemotactic agents.

Following seeding, the scaffold element-supported cells may be cultured under conditions which allow the formation of 3D structures. According to one embodiment, the scaffold element or the device comprising same is cultured under conditions which allow tissue formation.

The scaffold element-supported cells may be cultured for 1 day, two days, three days, four days, five days, six days, at least 1 week, 10 days or two weeks, three weeks, four weeks.

Additional agents may be incorporated into or on the scaffold of the present embodiments, along with the cells or tissue formed therefrom. Such agents include, but are not limited to those that promote cell adhesion (e.g. fibronectin, integrins), cell colonization, cell proliferation, cell differentiation, cell extravasation and/or cell migration. Thus, for example, the agent may be an amino acid, a small molecule chemical, a peptide, a polypeptide, a protein, a DNA, an RNA, a lipid and/or a proteoglycan.

According to another embodiment an antibody is incorporated on to the scaffold of the present invention. Preferably the antibody recognizes a cell-surface marker or a cell-secreted agent.

Proteins that may be incorporated into, or on the surface of the scaffolds of the present invention include, but are not limited to extracellular matrix proteins, cell adhesion proteins, growth factors, cytokines, hormones, proteases and protease substrates. Thus, exemplary proteins include vascular endothelial-derived growth factor (VEGF), activin-A, retinoic acid, epidermal growth factor, bone morphogenetic protein, TGFβ, hepatocyte growth factor, platelet-derived growth factor (PDGF), TGFα, IGF-I and II, hematopoetic growth factors, heparin binding growth factor, peptide growth factors, erythropoietin, interleukins, tumor necrosis factors, interferons, colony stimulating factors, basic and acidic fibroblast growth factors, nerve growth factor (NGF) or muscle morphogenic factor (MMP). The particular growth factor employed should be appropriate to the desired cell activity. The regulatory effects of a large family of growth factors are well known to those skilled in the art.

According to some embodiments of the present invention, the scaffold device further comprises a therapeutically active agent incorporated on or within the 3D polymeric element. According to some embodiments of the present invention, the scaffold device further comprises both cells and/or tissue and a therapeutically active agent.

The therapeutically active agent can be a biomolecule (e.g., a hormone, a factor, a growth factor, an antibody, a peptide, a protein, etc.), a drug, or any other agent that may improve tissue performance.

In some embodiments, the scaffold element comprises both a therapeutically active agent and cells and/or tissue formed therefrom.

According to some of any of the embodiments of the present invention the device comprises a therapeutically active agent in a releasable from, and the electrode structure is exposed to the therapeutically active agent, such that the therapeutically active agent is released upon transmission of stimulation signals through the electrode.

In some embodiments, the therapeutically active agent is associated, physically (e.g., by absorption or entrapment) or chemically (by e.g., electrostatic interactions), with the polymeric element, and the electrode structure is exposed to the polymeric material composing the polymeric element, such that the therapeutically active agent is released upon transmission of stimulation signals through the electrode to the polymeric material.

In some of such embodiments, the polymeric element comprises an electro-responsive polymeric material, as described herein, through which electric signal can be transmitted, and from which the therapeutically active agent can be released upon electric stimuli through the electrode in the electronic element. This enables delivering specific cues for tissue development or tissue control in order to improve function or performance of the tissue.

The use of electro-responsive hydrogel or polymer may provide controlled release of therapeutically active agent into the environment, providing spatially and temporally controlled cues to the tissue as well as providing needed aid to the tissue in event of distress. The environment can be, for example, the cellular microenvironment within the polymeric element, in case cells and/or tissue are comprised therein; and/or cells or tissue of a bodily organ that are engaged with the scaffold device.

The electro-responsive polymeric material is selected to bind a therapeutically agent by electrostatic interactions. Upon application of a suitable voltage (potential), the net charge of the polymeric material is altered, the electrostatic interactions are interrupted, and as a result, the therapeutically active agent is released to the environment (e.g., the cellular microenvironment).

In exemplary embodiments, the electro-responsive polymer is a positively charged polymer, as described herein, and the therapeutically active agent is a negatively charged agent.

Exemplary such agents include, for example, non-steroidal anti-inflammatory agents such as, but not limited to, salicylates, such as aspirin, Sulfosalycilic acid (SSA), disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; steroidal anti-inflammatory agents alpha-methyl dexamethasone, dexamethasone-phosphate, beclomethasone dipropionates, clobetasol valerate, desoxymethasone, desoxycorticosterone acetate, dexamethasone, dichlorisone, diflorasone diacetate, diflucortolone valerate, fluadrenolone, fluclorolone acetonide, flumethasone pivalate, fluosinolone acetonide, flucortine butylesters, fluocortolone, fluprednidene (fluprednylidene) acetate, flurandrenolone, hydrocortisone acetate, hydrocortisone butyrate, difluorosone diacetate, fluradrenolone, diflurosone diacetate, fluradrenolone acetonide, betamethasone and the balance of its esters, chloroprednisone, chlorprednisone acetate, hydrocortisone valerate, hydrocortisone cyclopentylpropionate, hydrocortamate, and beclomethasone dipropionate, triamcinolone; ATP, negatively-charged proteins, and Metamizole.

In other exemplary embodiments, the electro-responsive polymer is a negatively charged polymer, as described herein, and the therapeutically active agent is a positively charged agent.

Exemplary such agents include, for example, dopamine, norepinephrine, endrophonium, serotonins and other catecholamines, positively charged proteins, positively charged growth factors, and more. Any other positively-charged and negatively-charged small molecule and/or biomolecule (e.g., protein, peptides, nucleic acids, oligonucleotides) therapeutically active agents are contemplated.

In some embodiments, the therapeutically active agent is selected suitable for treating or repairing a damaged tissue or a condition associated with a damaged tissue, such as, but not limited to, an infracted myocardial tissue, as is further detailed hereinbelow.

Applications:

Any one of the devices described herein is usable for being implanted in, or on, or as a replacement of, a tissue or an organ, or part thereof, of a subject in need thereof. A device as described herein is therefore an implantable device according to some embodiments of the present invention.

In some of any of the embodiments described herein, the tissue or organ is one that contains electrically excitable cells and is subject to electrical stimulation in vivo.

The tissue can be, for example, cardiac muscle tissue, striated skeletal muscle tissue, smooth muscle tissue, bone, vasculature, or nerve tissue. Any other tissues or organs are contemplated, for example, liver or kidney. When the device is seeded with cells, the cells are preferably selected in accordance with the tissue or organ intended for implantation of the device therein or thereon.

Any one of the devices described herein is also usable for monitoring and/or stimulating an activity and/or a function of a cell. The cell can be a single cell, a plurality of cells or a tissue.

In some embodiments, the activity and/or function is an electrical activity or response to electric stimuli.

The cell or tissue can be such that is incorporated in the scaffold element of the device. A tissue can be formed by cultivating cell seeded in the scaffold element under suitable conditions.

Any one of the devices described herein is usable for monitoring and/or stimulating an activity and/or a function of the cell or the tissue incorporated in the device in vivo, upon implanting the device on or in or in replacement of a tissue or organ, or a part thereof, of a subject. This may be effected by receiving signals transmitted through the electrode, for monitoring the condition of the implanted device; or by transmitting signals through the electrode to the implanted device for stimulating an activity or function of the cell or tissue.

Thus, a method of monitoring or controlling a condition or function of an implanted tissue or cell is provided, which comprises implanting a scaffold device as described herein (which incorporates cells or tissue) and recording or transmitting signals (through one or more external electronic device(s)) to an incorporated cell or tissue through the electrode structure.

The advantage of using the scaffold device of the present embodiments for monitoring or controlling a condition or function of an implanted tissue or cell is that the same device can serve both for growing the tissue or cell prior to its implantation and for monitoring or controlling the condition or function of the tissue or cell, once implanted. Since the tissue or cell is grown in the presence of the electronic element, electrical communications of the tissue or cell as well as the polymeric element with the electrode(s) of the electronic element are readily established. Such electrical communications facilitate monitoring the condition or function of the tissue or cell via electrical signals received, directly or indirectly, from the tissue or cell, and also facilitate controlling the condition or function by electrically stimulating the tissue or cell, or by electrically inducing controlled release of agents from the polymeric element.

In embodiments in which the scaffold device comprises a plurality of electrodes, the distribution of electrodes can be used for characterizing a propagation (e.g., propagation path, propagation speed, propagation velocity) of a signal across the tissue, and/or for executing synchronized stimulation of the tissue at a plurality of different locations over the tissue. If desired, the plurality of electrodes can also be used for releasing an agent from the polymeric element from a plurality of location in a synchronized manner.

Any one of the devices described herein, which incorporates a therapeutically active agent, is usable for controlling a release of the therapeutically active agent from the polymeric element in the device, particularly is cases of a polymeric element which comprises an electro-responsive polymeric material.

This may be effected by transmitting a stimulating signal through the electrode of the device.

Thus, a method is provided for controllably releasing a therapeutically active agent as described herein to an implanted cell or tissue, which comprises implanting a device as described herein (which incorporates cells or tissue and the therapeutically active agent as described herein) and transmitting signals (through one or more external electronic device(s)) to an electro-responsive polymeric material composing the polymeric element through the electrode structure. Any one of the devices described herein, which incorporates a therapeutically active agent, is also usable for determining a performance (e.g., toxicity and/or efficacy) of a therapeutically active agent to a cell or tissue.

In some embodiments, determining a performance (e.g., toxicity and/or efficacy) of a therapeutically active agent to a cell or tissue may be effected by:

utilizing a device comprising a therapeutically active agent as described herein, and a cell or a tissue, both incorporated in the polymeric element, as described herein, preferably a polymeric element made of an electro-responsive polymer as described herein;

monitoring a function or activity of a cell or a tissue incorporated in the polymeric element (e.g., by recording electric signals transmitted by the electrode in the device); and comparing the monitored function or activity of the cell or the tissue with a monitored function or activity of the cell or the tissue without a therapeutically active agent, thereby determining a toxicity and/or efficacy of the therapeutically active agent to the cell or the tissue.

Determining can be effected in vitro or in vivo, in case the device is implanted in the subject.

Using this methodology, screening therapeutically active agents for toxicity or efficacy for a certain type of tissue or cells can be performed.

In some embodiments, such screening can be by preparing a series of scaffold devices, each incorporating in the polymeric element cells and/or tissues of a certain type, and each independently incorporating a different therapeutically active agent. A toxicity and/or efficacy of the therapeutically active agent to the cells or the tissue, upon electrical stimuli is then determined, and those agents which exhibits efficacy and do not exhibit toxicity are defined as lead candidates for, for example, repairing a function or activity of the cell or tissue, or promoting a function or activity of the cell or tissue.

In some embodiments, the function or activity is an electrophysiological function or activity.

The scaffold devices described herein (either alone or seeded with cells) may be used for modifying the electrophysiological function of excitable tissues. Thus, a scaffold device according to the present embodiments can be utilized to restore, enhance or suppress electrophysiological function across a tissue region thereby treating diseases caused by dysfunction in, or damage to, excitable tissues.

As used herein the term "treating" refers to inhibiting or arresting the development of a disease, disorder or condition and/or causing the reduction, remission, or regression of a disease, disorder or condition in a subject suffering from, being predisposed to, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

Examples of diseases and conditions which can be treated using the scaffolds of the present invention include, but are not limited to, glucose regulation disorders (e.g., diabetes mellitus), cardiac arrythmia (e.g., bradycardia, atrial fibrillation) diseases which are treatable by modulating (i.e., increasing or decreasing) the refractory period of a cardiac tissue (e.g., atrial fibrillation, atrial flutter, atrial tachycardia and ventricular tachycardia), diseases which are treatable by modulating (i.e., increasing or decreasing) neural excitability (e.g., epilepsy, Parkinson's disease and Alzheimer's disease) and diseases and conditions which are treatable by modulating (i.e., increasing or decreasing) pyramidal or purkinje cell coupling (e.g., cerebrovascular accident, epilepsy and pain (e.g., phantom pain).

According to a particular embodiment, the disorder is a cardiac disorder which is associated with a defective or absent myocardium.

Thus, according to another aspect of the present invention there is provided a method of treating a cardiac disorder associated with a defective or absent myocardium in a subject, the method comprising transplanting a scaffold device as described herein into the subject.

The method may be applied to repair cardiac tissue in a human subject having a cardiac disorder so as to thereby treat the disorder. The method can also be applied to repair cardiac tissue susceptible to be associated with future onset or development of a cardiac disorder so as to thereby inhibit such onset or development.

The present embodiments can be advantageously used to treat disorders associated with, for example, necrotic, apoptotic, damaged, dysfunctional or morphologically abnormal myocardium. Such disorders include, but are not limited to, ischemic heart disease, cardiac infarction, rheumatic heart disease, endocarditis, autoimmune cardiac disease, valvular heart disease, congenital heart disorders, cardiac rhythm disorders, impaired myocardial conductivity and cardiac insufficiency.

According to one embodiment, the method according to this aspect of the present invention can be advantageously used to efficiently reverse, inhibit or prevent cardiac damage caused by ischemia resulting from myocardial infarction.

According to another embodiment, the method according to this aspect of the present invention can be used to treat cardiac disorders characterized by abnormal cardiac rhythm, such as, for example, cardiac arrhythmia.

As used herein the phrase "cardiac arrhythmia" refers to any variation from the normal rhythm of the heart beat, including, but not limited to, sinus arrhythmia, premature heat, heart block, atrial fibrillation, atrial flutter, pulsus alternans and paroxysmal tachycardia.

According to another embodiment, the method according to this aspect of the present invention can be used to treat impaired cardiac function resulting from tissue loss or dysfunction that occur at critical sites in the electrical conduction system of the heart, that may lead to inefficient rhythm initiation or impulse conduction resulting in abnormalities in heart rate.

The method according to this aspect of the present invention is effected by transplanting a scaffold device as described herein to the heart of the subject.

As used herein, "transplanting" refers to providing the scaffold of the present invention (with or without cells), using any suitable route. This term is used herein interchangeably with "implantation" or "implanting".

In some embodiments, implantation of a scaffold device as described herein is performed while using the scaffold device as described herein in a form of a patch, such as, but not limited to, a cardiac patch. For example, a cardiac patch can be provided by growing an engineered cardiac tissue using the polymeric element as a scaffold. The polymeric element can have a surface configured to be joined to the surface of the host heart such that the engineered cardiac tissue contacts the tissue of the host heart.

Similarly, the scaffold device can be configured to be joined to a surface of other host organs, including, but not limited to, a host liver, a host skin, a host kidney, a host pancreas, etc.

The devices, systems and methods or uses described herein can be utilized in a variety of different manners. The device can be fabricated and utilized in many different configurations so as to adapt it to the intended use, whether it be a different kind of tissue (e.g., cardiac, liver, kidney etc.), a different kind of injury (e.g., different sizes and types of myocardial infarctions, etc.), different kinds of experiments (e.g., drug testing, injury control, release protocols etc.), and different types of monitoring (e.g., action potential, stimulation, factor/drug release).

The System:

FIG. 30 is a schematic illustration of a system 300 for controlling, treating and/or extracting information from cells and/or tissue incorporated in a scaffold element of a device, according to some embodiments of the present invention. System 300 comprises scaffold device 280 and one or more electric devices 302, 304. For example, device 302 can be a controller configured to transmit signals through the electrode(s) of scaffold device 280, and device 304 can be a measuring device configured for receiving signals conveyed via the electrodes of scaffold device 280. Signals received from the electrode(s) are optionally and preferably digitizing for example, by device 304 or an external analog-to-digital (A2D) circuit 310. Signals transmitted to the electrodes are optionally and preferably analog signals. In some embodiments of the present invention device 302 generates digital signals which are thereafter converted into analog signals for example, by device 302 or an external digital-to-analog (D2A) circuit 312.

Any of devices 302 and 304 can include a power source or they can be connected to an external power source. In some embodiments system 300 comprises device 302 but not device 304, in some embodiments system 300 comprises device 304 but not device 302, and in some embodiments system 300 comprises both device 302 and device 304. Preferably, each of devices 302 and 304 communicates separately with each of the electrodes of scaffold device 280 thereby allowing transmitting or receiving different signals (and/or different timings) to or from different locations over the scaffold element. In some embodiments of the present invention a coded interface (not shown) receives different signals from different electrodes and transmits each of at least some of the different signals to the measuring device 304. A coded interface can also be used for transmitting different signals through different electrode structures. Also contemplated, is the use of a multiplexer, for combining two or more communication channels originated from the electrodes.

Any of devices 302 and 304 can be provided as a data processor, such as a general purpose computer or dedicated circuitry, configured to transmit and/or receive signals from the electronic element. When the data processor receives signals from the electronic element, the data processor is preferably supplemented by a computer software product that allows the processor to process the signals and provides data pertaining to the environment in which the exposed part(s) of the electrode structure is present. The data can be displayed on a display device or transmitted to a computer readable medium. The processing can be done immediately after the acquisition of the signals by the electronic element (e.g., within less than 1 hour or within less than 1 minute or within less than 1 second or within a few milliseconds), or it can be done off line. When the processing is done off line, the signals are preferably recorded in a digital or analog form on a storage medium as known in the art.

According to some embodiments of the present invention system 300 comprises an amplifier 306 configured for amplifying signals transmitted through the electrode(s). Optionally and preferably the electrode(s) is connected to the amplifier 306 via a pre-amplifier circuit 308. Amplifier 306 and/or pre-amplifier 308 can be provided separately from devices 302 and 304 or they can be integral parts thereof. Also contemplated, are embodiments in which amplifier 306 and/or pre-amplifier 308 are integral parts of scaffold device 280.

FIGS. 1A-B illustrate an operation principle of an exemplary system according to some embodiments of the invention. The system comprises scaffold device 280 as described herein, that combines both a porous substrate allowing continuous and confluent tissue assembly. In the exemplified illustration, the scaffold device incorporates cardiomyocytes cultivation. The electrodes 286 are distributed throughout the scaffold element 282 for stimulating the tissue and/or conveying signals from the tissue and/or for actuating release of an agent (e.g., drug or factor) loaded onto scaffold element 282. A computer 302/304 may serve both as a controller and as a measuring device, wherein stimulating and/or actuating signals can be transmitted by the computer and information signals from the tissue can be recorded and/or displayed by the computer.

The system of the present embodiments can serve both as a scaffold for (e.g., cardiac) tissue generation and for monitoring and controlling an implanted engineered tissue from outside. The ability to electrically control the tissue allows recording (monitoring), stimulating and controlling/stimulating drug release from (e.g., electrically responsive) polymers molded onto the electrodes.

Fabrication:

A device as described herein can be fabricated by fabricating the electronic element as desired (for example, as described in the Examples section the follows) and depositing/molding thereon a 3D polymeric element as described herein.

In some embodiments, the formation of the polymeric element is performed in the presence of the electronic element. In exemplary such embodiments, the polymeric element is formed by electrospinning, and the electrospinning is performed in the presence of the electronic element, such that the electrospun polymeric material is formed on the electronic component. In other exemplary embodiments, the formation of the polymeric element is performed by electropolymerization of an electropolymerizable polymer, while using the electronic element as a working electrode.

In some embodiments, a polymeric element is formed and is then deposited o molded onto or around the electronic component. In exemplary such embodiments, a hydrogel or a lyophilized hydrogel is deposited in the electronic element by means of, for example, a micromanipulator or blotting from a volatile liquid solution, as exemplified hereinafter.

General:

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Electrospinning was performed as described hereinbelow.

A 4" simple silicon wafer was obtained from University wafers.

SU-8 3005 and SU-8 3025 photoresists were obtained from Microchem.

AZ5214E, AZ726 and Propylene glycol monomethyl ether acetate (PGMEA) was obtained from microchemicals.

PCL, gelatin, albumin, poly(2-acrylamido-2-methylpropane sulfonic acid-co-n-butylmethacrylate) and polypyrrole, were obtained from Sigma Aldrich (MO, USA).

Other chemicals were obtained as indicated below.

All other chemicals were obtained from known vendors.

Rat neonatal ventricular cardiomyocytes were obtained from Harlan, Israel, and were grown growth medium M-199 (Biological Industries).

SEM measurements were performed using JEOL model JSM-840A.

Fluorescent microscopy was performed using a fluorescence microscope (Nikon Eclipse TI), and immunostaining. A device incorporating cardiac cells in a fibrous scaffold, prepared as described herein, was treated by fixing and permeabilizing the cells in 100% cold methanol for 10 minutes. The device was thereafter washed three times in DMEM-based buffer and then cells were blocked for 1 hour at room temperature by incubating with DMEM-based buffer containing 2% FBS, after which the samples were washed three times. The samples were then incubated with primary antibodies to detect α-sarcomeric actinin (1:750, Sigma-Aldrich), troponin (1:200, Abcam), and vimentin (1:100, Invitrogen, Carlsbad, Calif.), washed three times and incubated for 1 hour with Alexa Fluor 647 conjugated goat anti-mouse antibody (1:500; Jackson) and Alexa Fluor 488 conjugated goat anti-rabbit antibody (1:500; Jackson). For nuclei detection, the samples were incubated for 3 minutes with Hoechst 33258 (1:100; Sigma) and washed three times.

Example 1

Fabrication of an Electronic Element

The following presents a general procedure for fabricating an electronic element according to some embodiments of the present invention.

A thin metal sacrificial layer is sputtered, using photolithography and metal evaporation to create nets of photoresist and electrodes, as exemplified in FIGS. 2A-B. A mask used during photolithography gives the electronic components its shape. The electrodes are exposed only in small pads at one end and to a connector at the other end, as exemplified in FIG. 3. The connector is designed so as to fit into a Multi Channel Systems pre-amplifier to allow signal transduction to and from an amplifier and/or to and from a computer.

The following describes exemplary procedures for preparing exemplary electronic elements according to some embodiments of the present invention.

A 4" simple silicon wafer was cleaned by $N_2$, and a 10 nm layer of Ni was deposited thereon by vapor evaporation, forming a sacrificial layer. Then, a 5 micron thick layer of pre-baked SU-8 3005 photoresist, as a polymeric layer, was deposited by spin coating onto the wafer, and was cross-linked by UV exposure through a an in-house made photolithography mask that gives the device its shape. Thereafter, the photoresist was baked again, developed in PGMEA and cured at a high temperature to achieve final strength.

Then, a very thin layer of AZ5214E photoresist was deposited by spin coating and baked, cross-linked by UV with a mask that defines the electrodes on the device, baked again and fully exposed to UV for a long time without a mask to reverse the pattern, and then developed in AZ726.

Thereafter, a 5 nm of Cr and 200 nm of Au are evaporated onto the device and the device is allowed to soak in NMP for 24 hours to remove all the Cr and Au from areas where electrodes are not defined. At the end, another 20 microns thick layer of SU-8 3025 photoresist is deposited by spin coating onto the device, baked, cross-linked by UV with a third mask defining the passivation of the electrodes and then baked, developed in PGMEA and cured in a high temperature.

The whole wafer was then soaked in 21% nitric acid to allow the bottom Nickel layer to etch and release the device. The device was then washed and dried gently.

FIGS. 2A-B present photographs of the released electronic element. The gold electrodes are plainly visible, and are fully passivated throughout their length and only exposed at both edges (tips) to allow contact with the tissue and e.g., a pre-amplifier.

FIG. 3 presents a microscope image of an exposed tip of a gold electrode within an exemplary electronic element. The dimensions of this exemplary exposed tip are about 30 minrons.

Generally, a dimension of the exposed tip may range from 1 to 100 microns, or from 1 to 50 microns, or from 10 to 50 microns.

Example 2

Fabrication of a 3D Polymeric Element in Association with the Electronic Element An electronic element prepared, for example, as described in Example 1, is covered with a polymeric material, as described in any one of the respective embodiments herein to generate a scaffold, e.g., a three dimensional scaffold or three dimensional polymeric element, for promoting cell adhesion and tissue generation, as exemplified in FIGS. 4 and 5A-B.

In an exemplary process, a fibrous scaffold is generated by electrospinning. Briefly, electrospinning is performed by injecting a solution of a polymer (such as, but not limited to, protein, synthetic polymer, natural polymer, or any other polymer as described herein in any one of the respective embodiments and any combination thereof) in a solvent through a needle into a strong (several to 30 kV) electric field where one electrode is attached to the needle and the ground is attached to a conducting collector. The strong electric field and repulsion forces of the solvents in the field make the polymer stretch to sizes of up to tens of nanometers and collect on the collector. The device is laid on the collector and the fibers are spun on it from one side and then the other.

Alternatively, a hydrogel scaffold or other 3D scaffolds are prepared, using methodologies known in the art, such as decellularization of natural matrices, free radical polymerization or electropolymerization.

Then, optionally, cells (e.g., cardiomyocytes) are seeded onto the scaffold and the scaffold is incubated under suitable conditions to allow tissue generation, as exemplified in FIGS. 6 and 7A-B. Different cells can be seeded, to provide different types of tissue generation. Exemplary such cells are neurons. Seeding and culture conditions (during incubation) are selected suitable for the selected cells.

The following describes exemplary procedures for further treating the obtained electronic device by depositing thereon a polymeric material, such as a 3D scaffold.

In one exemplary procedure, a mixture of PCL and Gelatin, which is both strong and promotes cell attachment and tissue generation, was deposited onto the device by a process of electrospinning.

Briefly, 10% gelatin (Sigma, St. Louis, Mo.) and 10% PCL (Sigma, St. Louis, Mo.) were separately dissolved in 2,2,2-trifluoroethanol (Acros, Belgium) overnight at room temperature. The next day, the solutions were mixed in the ratio of 1:1. Using a syringe pump (Harvard apparatus, Holliston, Mass.), the polymer solution was delivered through a stainless steel 20G capillary at a feeding rate of 0.5 mL $h^{-1}$. A high voltage power supply (Glassman high voltage inc.) was used to apply a 10 kV potential between the capillary tip and the collector, positioned 10 cm beneath the tip.

An electronic component produced as described in Example 1 hereinabove (see, for example, FIGS. 2A-B) was laid on the collector and the fibers were spun on it from one side and then the other.

In another exemplary procedure a scaffold containing albumin was deposited onto the device by a process of electrospinning.

Bovine serum albumin [BSA; Fraction V, MP Biomedicals, Aurora, Ohio; 10% and 14% (w/v)] was dissolved in TFE and distilled water (9:1, respectively), following with addition of excess β-mercaptoethanol (Merck, Darmstadt, Germany) for overnight reaction. The solution was electrospun at room temperature, using a syringe pump (Harvard Apparatus) delivered at a rate of 2 mL/h. A high voltage supply was used to apply a 12 kV potential between the capillary tip and the grounded aluminum collector placed at a distance of 14 cm. Randomly oriented scaffolds were collected on a round plate of 13 cm in diameter. Aligned scaffolds were collected on a rotating vertical wheel of 20 cm in diameter and 1 cm in thickness. The scaffolds were dried under vacuum, and further kept in a desiccator. Fiber diameter and pore size were measured using ImageJ (NIH).

An electronic component produced as described in Example 1 hereinabove (see, for example, FIGS. 2A-B) was laid on the collector and the fibers were spun on it from one side and then the other. FIG. 4 presents an image of the electronic element shown in FIGS. 2A and 2B after PCL/Gelatin nanofibers have been electrospun on it to form a scaffold to allow tissue organization.

FIG. 5A presents a scanning electron micrograph (SEM) of an electrode structure comprising a gold electrode coated by SU-8, as presented in FIGS. 2A-B, and covered by PCL/gelatin fibrous scaffold.

FIG. 5B presents a scanning electron micrograph (SEM) of an electrode structure comprising a gold electrode coated by SU-8, as shown in FIGS. 2A-B, and covered by albumin fibrous scaffold.

A device thus prepared was then washed to allow removal of all acids and solvents and cell seeding for tissue generation was performed, using rat neonatal ventricular cardiomyocytes. The device was incubated in an appropriate medium and conditions for 3-7 days, for tissue generation. The final device is also referred to herein as "cyborg tissue".

Cardiac cells were isolated according to Tel Aviv University ethical use protocols as previously described (Dvir et al., 2006 Tissue Eng 12(10):2843-2852.). Briefly, left ventricles of 0-3-day-old neonatal Sprague-Dawley rats were harvested and cells were isolated using six cycles (30 minutes each) of enzyme digestion with collagenase type II (95

U/mL; Worthington, Lakewood, N.J.) and pancreatin (0.6 mg/mL; Sigma-Aldrich) in Dulbecco's modified Eagle Medium (DMEM, $CaCl_2.2H_2O$ (1.8 mM), KCl (5.36 mM), $MgSO_4.7H_2O$ (0.81 mM), NaCl (0.1 M), $NaHCO_3$ (0.44 mM), $NaH_2PO_4$ (0.9 mM)). After each round of digestion cells were centrifuged (600G, 5 minutes) and re-suspended in culture medium composed of M-199 supplemented with 0.6 mM $CuSO_45.H_2O$, 0.5 mM $ZnSO_4.7H_2O$, 1.5 mM vitamin B12, 500 U/mL Penicillin and 100 mg/mL streptomycin, and 0.5% (v/v) FBS. To enrich the cardiomyocytes population, cells were suspended in culture medium with 5% FBS and pre-plated twice (30 minutes). Cell number and viability was determined by hemocytometer and trypan blue exclusion assay.

A device covered with electrospun Albumin fibers was seeded with $10^6$ neonatal rat ventricular myocytes, and the cells were allowed to grow for 4-5 days, in the presence of a M-199 growth medium supplemented with 0.6 mM $CuSO_45.H_2O$, 0.5 mM $ZnSO_4.7H_2O$, 1.5 mM vitamin B12, 500 U/mL Penicillin and 100 mg/mL streptomycin, and 5% (v/v) FBS.

FIG. 6 presents an image of an electronic element as shown in FIGS. 2A-B covered with PCL/gelatin fibers after it has been seeded with cardiomyocytes, as described hereinabove. The device when free-standing is flexible and retains its electrical properties while being able to serve as a scaffold for tissue generation.

FIG. 7A presents a fluorescent microscope image of rat neonatal ventricular cardiomyocytes seeded on a device as shown in FIG. 6. The cells are elongated and show massive actin striation indicative of mature tissue formation and cell-cell and cell-matrix interactions. It is shown that cells grow directly on the gold electrodes. This connection enables the electrodes to sense action potentials generated from the tissue and transmit electrical stimuli to the tissue.

FIG. 7B presents a fluorescent microscope image of rat neonatal ventricular cardiomyocytes seeded on a device having an electrospun albumin as a polymeric element, as shown in FIG. 5B.

Example 3

In Vivo Implantation

FIG. 9 is a photograph showing subcutaneous implantation of an engineered (cyborg) tissue (a device seeded with cells, upon tissue formation) according to some embodiments of the present invention into a Sprague-Dawly rat.

A Sprague-Dawly rat was anesthetized, a small patch from its back was shaved and then a small incision was made and the device was placed therein subcutaneously, as shown in FIG. 9. The device was placed such that the electrode array is inside the animal while the connector to the amplifier protrudes from the skin. Stitches were made to both sides of the connector and glue was used to strengthen the device's position in the animal and help close up the wound.

After allowing a few days to recover the animal was again anesthetized and the device was connected to the computer through the same system as before. FIG. 10 is a photograph showing recording action potentials and actuating the implanted engineered (cyborg) tissue, upon sedating the animal and connecting it to a pre-amplifier.

Example 4

In Vitro Assays—Monitoring and Stimulating

FIG. 8 presents an exemplary system set up for electrical signal readings. The engineered (cyborg) tissue is connected to an adaptor and into a miniature pre-amplifier and then into another filter/amplifier, from there it goes into a main digitizing unit and into a computer for data analysis.

After the device was incubated for a time period that allows tissue generation, the obtained cyborg tissue was connected to the pre-amplifier and monitored through the computer, using a system as exemplified in FIG. 8. This allows monitoring the progress of tissue formation as well as studying the influence of different conditions and substances on the tissue, an approach that could replace animal drug testing and make it easier and simpler. In an exemplary assay, a device, as shown for example, in FIG. 5B, having an electrospun albumin fibers as the 3D polymeric element in association with the electronic element as shown in FIGS. 2A and 2B, was seeded with $10^6$ neonatal rat ventricular myocytes, and the cells were allowed to grow for 4-5 days, in the presence of a M-199 growth medium supplemented with 0.6 mM $CuSO_45.H_2O$, 0.5 mM $ZnSO_4.7H_2O$, 1.5 mM vitamin B12, 500 U/mL Penicillin and 100 mg/mL streptomycin, and 5% (v/v) FBS.

At the time of the recording, the device was connected to a ME64-FAI-MPA-System by multichannel systems (Germany). Action potentials were recorded using the MC rack software which allows recording over multiple electrodes simultaneously.

After action potentials were recorded, 100 nM of noradrenaline was added to the growth medium and the device was allowed to incubate for 15 minutes after which the device was reconnected and action potentials were again recorded.

FIGS. 11A-B present action potentials recorded from a single (FIG. 11A) and multiple (FIG. 11B) electrodes in the above-described assay. The use of multiple electrodes allows calculating signal velocity and locating problems in specific areas. The action potentials recorded upon subjecting the cyborg tissue to a stimulating drug were also recorded.

FIG. 12 presents action potentials recorded from a single electrode of the device cultured with neonatal rat ventricular cardiomyocytes. The top shows the action potentials before adding a stimulating drug (Noradrenalin) and the bottom shows the action potentials recorded after the addition of the drug. As shown, the frequency of the action potentials has increased due to the response of the tissue to the drug.

Since the electrodes are integrated within the tissue in a variety of different arrays, generating electric pulses and stimulating specific regions in the engineered tissue are enabled. This allows pacing the tissue as well as aiding in tissue formation.

The influence of electrical stimulation from within the device was tested. A device, as shown for example, in FIG. 7B, having an albumin fibrous scaffold in association with the electronic element as shown in FIGS. 2A and 2B, and cultured with neonatal rat ventricular cardiomyocytes, was incubated with a fluorescent calcium probe that fluoresces when the tissue contracts.

In brief, the device was incubated with 10 µM fluo-4 AM (Invitrogen) and 0.1% Pluronic F-127 for 45 minutes at 37° C. and then washed in Tyrodes solution 3 times. The calcium transients were imaged using Nikon eclipse Ti inverted research microscope. The images were acquired with a Hamamatsu ORCA—flash 4.0 camera at 100 frame/s with 3 µm/pixel spatial resolution. Intensity of fluorescence over time was measured using ImageJ software. The cells were stimulated using an STG-4002 stimulus generator from multichannel systems with 50 ms long, 3 volts strong pulses.

Fluorescence was measured throughout ten different points in the cultured tissue.

FIGS. 13A-B present the data obtained. FIG. 13A presents the tissue before stimulation, showing sporadic contractions throughout the tissue and no synchronized contractions. FIG. 13B is after the tissue was stimulated at a 1 Hz pace from within the device. All measured points are synchronized and contract together as can be observed from their convergent peeks.

Example 5

Drug-Releasing Devices Having Electro-Responsive Polymers

In some embodiments of the present invention, the three dimensional polymeric element is formed from an electro-responsive polymer. In these embodiments, a drug can be in association with the polymeric matrix, through, for example, electrostatic interactions, and be released therefrom upon electric stimulation.

FIG. 14 presents a schematic illustration of such a device. Upon application of electric power, the drug is released from the electro-responsive polymer that is in contact with the electronic element.

The following describes exemplary procedures for depositing drug-releasing positive and negative electro-responsive polymers:

Preparation of a PolyAMPS (Negative Polymer) Hydrogel:

2-acrylamido-2-methylpropanesulfonic acid (AMPS) and n-butylmethacrylate (BMA) were purchased from Acros (Belgium). Cross linkers N'N' methylenebisacrylamide (MBMA), initiators Tetra methyl ethylene di-amine (TEMED), Ammonium presulfate (Aps) and Drug model Dopamine & Norepinephrine were purchased from Sigma (St. Louis, Mo., USA). DMF was purchased from Bio lab, Israel and NaOH (Merck, Germany) was used as a solution. All materials were used as received.

A series of cross-linked random copolymers poly(AMPS/BMA) was synthesized by using MBMA as a cross linker (0.8, 1.2, 1.6 mole % of the monomers) and a mixture of APS and TEMED (10:1 V/V %) as an initiator (0.05, 0.075, 0.1 mole % of the monomers). The monomers composition ratio AMPS/BMA was a 27/73 mole ratio.

A mixture of monomers, initiator and cross linker was dissolved in DMF (190 mole % of the monomers). Polymerization was performed in PCRs conical tubes at 60° C. for 3 days. After polymerization, the polymers were removed from the test tubes and washed in a water/acetone (50/50 v/v %) solvent mixture to extract unreacted compounds. The solvent was replaced daily for a week. After the hydrogel reached equilibrium, it was dried either by lyophilization, at ambient conditions (atmosphere) or at hood conditions, as detailed hereinbelow.

Hydrogels loaded with a drug (e.g., dopamine or norepinephrin) were prepared by treating the obtained co-polymer with a NaOH solution, so as to form a sodium salt of the sulfonic acid groups, and reacting the obtained salt with a saturated solution of the drug.

In brief, after the hydrogel was dried, it was mixed, for three days, in NaOH aqueous solution (2 M) in 15 ml test-tube. This process converts the —$SO_3H$ group to —$SO_3Na$. Afterwards, a similar process was used by placing the hydrogel in a half-saturated aqueous solution of the drug (0.2 M), which converted the —$SO_3Na$ group to —$SO_3D$ (where D is an indication for the drug group).

The dried hydrogel is deposited in the electronic element by means of a micromanipulator or by immersing the hydrogel in a volatile liquid and then blotting it onto the electronic element. In brief, the gel is cut into very small pieces and dispersed in acetone at a very low concentration. A 0.5 microliter drop is placed on the electrode and is allowed to dry. Microscopy is used to determine if the gel is appropriately located.

Optionally, a layer of electrospun polymeric material (e.g., albumin) is then deposited.

Preparation of Polypyrrole (Positive Polymer) Hydrogel:

Pyrrole was at room temperature in a 10-mL one-compartment cell, using an electrochemical workstation under computer control. The gold-based microelectrodes, prepared as described in Example 1 hereinabove, were used as working electrodes. The counter electrode was platinum wire and the reference electrode was a saturated calomel electrode (SCE). The electrolyte was an aqueous solution (100 ml) containing 0.2 M pyrrole (1.39 ml) and 0.2 M sulfosalicylic acid (5.08 grams), which was degassed by nitrogen stream before polymerization was effected. The SSA-doped PPy films (PPy-SSA) were prepared on the gold microelectrodes by galvanostatic polymerization using a current density of 2.5 mA/$cm^2$ for 800 seconds. The as-prepared PPy-SSA films were rinsed with de-ionized water and dried in air at room temperature. A second layer was thereafter deposited by using an aqueous solution (100 ml) of 0.2 M pyrrole and 0.1 M NaCl (0.5844 grams), subjected to a galvanostatic polymerization with a current density of 2 mA/$cm^2$ for 500 seconds.

FIG. 15A presents a SEM image of a bare electronic element as described in Example 1 (top image) and an image obtained by fluorescent microscopy after (bottom image) deposition of PolyAMPS polymer loaded with the fluorescent substance—Fluorescein. Fluorescein was loaded into the polymeric element by placing the gel is a solution containing the fluorescein.

The release profile of dopamine from device polymeric element made of a positive electro-responsive polymer as described herein was measured as follows:

Disc shaped preloaded slices of formed hydrogel (2-3 mm) were placed between two Graphite electrodes (1 cm apart) in a plastic culture plate. The electrodes were connected to a stimulus generator (STG-4002 multichannel systems, Germany), and the plate was filled with a medium of PBS (0.35 ml). A DC pulse of different intensities (0-8 volt) and different durations (0-15 minutes) was supplied.

Nano-Drop spectrophotometer (ND-1000 spectrophotometer, Thermo scientific, Wilmington Del. U.S.A) at a wave length of 462 was used to examine the light absorbance of the medium. The relation between the light absorbance and the concentration is given by Beer-Lambert as a linear equation:

$$A=\varepsilon l c$$

wherein A is the light absorbance, l is the length of the light through the sample [m], C is the concentration in [M], and $\varepsilon$ is the molar absorptivity [$m^{-1}M^{-1}$].

FIG. 15B presents the release profile of dopamine from a poly(2-acrylamido-2-methylpropane sulfonic acid-co-n-butylmethacrylate) scaffold, as described herein, as measured by optical density. The arrows showing the time points at which voltage was applied to the device. An on-off behavior of the drug release is clearly shown, with a much higher drug release rate when voltage is applied (on) than when it is not applied (off).

FIG. 16 presents a scanning electron micrograph (SEM) of a positive electro-responsive polymer, polypyrrole, deposited on a gold electrode with a TiN layer, prepared as described in Example 6 hereinafter.

The release profile of Sulfosalicylic acid (SSA) from the polypyrrole hydrogel scaffold was measured by Nano-Drop spectrophotometer (ND-1000 spectrophotometer, Thermo scientific, Wilmington Del. U.S.A), as described hereinabove, at a wave length of 280 nm.

FIG. 17 shows the release profile of SSA from a polypyrrole scaffold. The on-off behavior is shown herein too. When voltage is applied the drug is released into the polymer's vicinity and when voltage application is discontinued drug release ceases.

Example 6

Electrodes Having Titanium Nitride Deposited Therein

Titanium Nitride was utilized for improving the quality of the action potentials recorded from the device. Titanium nitride has a columnar rough surface topology and thus increases its contact area with the cells. It is also characterized by high charge transfer abilities, such that the amount of charge transferred in its presence is increased compared to a gold electrode as described hereinabove.

A device having a TiN layer was fabricated as described in Example 1 hereinabove, with the following addition:

After deposition of gold and chromium, and the following lift off, a second layer of AZ5214E was deposited and exposed using a specific mask. A layer of 100 nm thick TiN was thereafter deposited using Radio frequency sputtering. The electrode shape was achieved by immersing the devices in NMP overnight to allow all unexposed AZ5214E and TiN to dissolve.

FIG. 18 describes a profile measurement of TiN deposited on gold electrodes, with the "rough" areas presenting the profile for areas covered with titanium nitride and the flat area are of the gold electrodes (without TiN overlayer).

Example 7

Curved Devices

The effect of the electrode's shape, particularly curvature, on its conductance was measured.

Measurements of conductance were performed using a Keithly probe station with two probes. The conductance was measured as a function of voltage between −5 and 5 volts. All conductances were compared to the original straight unrolled device. Rolling was effected manually around cylindrical devices with varying diameters. All devices were the same as original.

FIG. 19 shows the conductance of a device as shown in FIGS. 2A-B, as a function of the radius of curvature. The bar graph shows that conductivity is maintained substantially the same for all curvature radii tested, this demonstrating that the device is robust and maintains its electrical properties also under strain.

It is to be noted that the polymer (e.g., photoresist) used for coating the electrode can be selected so as to impart different properties to the device. Polyimide, for example, can be used for the fabrication process in order to impart, for example, a better stretching ability to the device.

FIG. 20 presents a schematic illustration of an electronic element, designed to include structural features that will allow for stretching motions. The electrodes are designed so that they have a curled morphology instead of a linear one so that it can be stretched while retaining its properties.

Example 8

Controlling Drug Release Parameters

The effect of various process parameters on the drug release properties of the drug-loaded electro-responsive hydrogels described herein, was evaluated.

All fabrication processes were the same as described hereinabove for a negative electro-responsive polymer (see, Example 5), except that after gel formation, the hydrogel were rinsed in water and acetone for several days to allow monomers to be removed and then allowed to dry in different environments (either in an ambient environment, in a chemical hood or by lyophilization). Drug loading was performed as described hereinabove, after the drying. Drug release was measured as described hereinabove. Diffusion was measured similarly, but without applying any electric field. Again samples were taken every 5 minutes and measured using a nano-drop spectrophotometer, operated at 462 nm.

FIG. 21 presents comparative plots showing the effect of the drying method of the release profile of the drug from the dried hydrogel by diffusion. As shown, the drying method affects the diffusion rate, presumably due to the different pore sizes of the hydrogel in each of these methods.

FIG. 22 presents comparative plots showing the effect of the drying method of the release profile of the drug from the dried hydrogel upon electric stimulation. As shown, the drying method affects the release rate upon electric stimulation, yet, a different release pattern is observed as compared to the diffusion rate.

FIG. 23 presents a graph showing the long-term release profile of the drug from the dried hydrogel upon electric stimulation, in a hydrogel dried by lyophilization. Stimulation was applied daily on the gel and the amount of drug released was measured.

FIG. 24 presents comparative plots showing the drug release profile as a function of the applied potential, from a hydrogel dried by lyophilization.

Example 9

Swelling and Drug Loading

The effect of the molar ratio of the initiator and cross-linking agent and the drying method on the swelling capacity of an electro-responsive negative polymer loaded with dopamine, was tested and the effect of the molar ratio of the initiator and cross-linking agent on the drug loading was also tested. The hydrogel was fabricated as described in Example 5 hereinabove.

Swelling Degree Measurements:

After drying, two pieces from the hydrogel were cut and placed in a KCl/HCl buffer (pH 2) and at PBS1 solution to mimic physiological conditions. The Weight Swelling Fraction was calculated by the equation:

$$WSF\ \% = \frac{W_s - W_d}{W_d} \times 100$$

wherein $W_d$, $W_s$ is the weights of the dry hydrogel and the swelling hydrogel, respectively.

FIG. 25 presents a bar graph showing the swelling degree of the gels as a function of the molar ratio of cross linker and initiator used during gel polymerization.

FIG. 27 presents a bar graph showing the effect of the drying method on the swelling capacity of the hydrogel, and show higher swelling in the lyophilized hydrogel.

Drug Loading Measurements:

The amount of drug loaded into the gel as a function of the molar ratio of the initiator and the cross-linking agent used in the polymerization was measured The effect of the molar ratio of the initiator and cross-linking agent on the drug loading into an electro-responsive negative polymer loaded with dopamine was tested. The hydrogel was fabricated as described in Example 5 hereinabove. Drug loading was measured by sampling the drug concentration in the loading solution during the loading process. FIG. 26 presents a bar graph showing the amount of drug loaded into the gel as a function of the initiator/cross-linking agent molar ration.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A scaffold device comprising:
   a three-dimensional polymeric element in a form of a network of microfibers or nanofibers, said polymeric element comprising an electro-responsive polymeric material that undergoes a change in its electronic structure upon application of voltage;
   an electronic element being integrated with said polymeric element,
   cells incorporated in and/or on said polymeric element, to form an engineered tissue, and
   a therapeutically active agent, incorporated in and/or on said polymeric element, and being associated with said electro-responsive polymeric material via electrostatic interactions, to allow release of said agent to said incorporated cells responsively to application of voltage;
   said electronic element comprising a plurality of electrodes, each electrode being individually connectable to a measuring device and/or a controller,
   wherein at least one electrode of said plurality of electrodes comprises a conductive core, an electrically-isolating layer, and a nanometric layer of electrically-conductive material sputtered to partially coat the core so as to impart roughness at selected areas of said core, and wherein said electrically-isolating layer is deposited such that a portion of said at least one electrode remains partially uncoated in a plurality of discrete locations over said at least one electrode and is exposed to an environment surrounding said at least one electrode at each location of said plurality of discrete locations.

2. The device of claim 1, wherein said at least one electrode is exposed to said environment at a tip of said at least one electrode.

3. The device of claim 1, wherein said thin electrically-isolating layer is an electrically-isolating polymeric layer.

4. The device of claim 1, wherein said thin electrically-isolating layer has a thickness that ranges from 0.1 micron to 100 microns.

5. The device of claim 1, wherein at least one dimension of said at least one electrode ranges from 1 micron to 1000 microns.

6. The device of claim 1, wherein said at least one electrode has a shape of a straight line or of a curved line.

7. The device of claim 6, wherein said at least one electrode is elastic.

8. The device of claim 1, wherein each electrode is individually connectable to said controller and wherein said controller is configured for transmitting stimulation signals through said at least one electrode.

9. The device of claim 1, further comprising a miniature power source mounted in proximity to said electronic element.

10. The device of claim 1, wherein each electrode is individually connectable to said measuring device, and wherein said measuring device is configured for measuring signals transmitted from the polymeric element through said at least one electrode and/or for measuring signals transmitted from said environment through said at least one electrode.

11. The device of claim 1, wherein said polymeric element comprises a synthetic polymer.

12. The device of claim 1, wherein said polymeric element comprises an electrospun fibrous polymeric material.

13. The device of claim 12, wherein said polymeric material comprises at least one of albumin, a polycaprolactone (PCL), gelatin, a poly(lactic acid) (PLA), a poly(lactic acid-co-glycolic acid) (PLGA), decellularized extracellular matrix and any combination thereof.

14. A system comprising the device of claim 1 and at least one electric device selected from a group consisting of said controller and said measuring device.

15. A method of implantation, comprising:
    implanting the scaffold device of claim 1 in an organ; and
    receiving electrical signals from said cells via said electronic element.

16. The method of claim 15, further comprising transmitting stimulating signals via said electronic element so as to controllably release said therapeutically active agent from said polymeric element.

17. The method of claim 15, wherein said cells are responsive to electrical stimulation and the method comprising transmitting stimulating signals via said electronic element so as to stimulate said cells.

18. A method of treating disease or disorder caused by dysfunction in, or damage to, an excitable tissue in a subject in need thereof, the method comprising transplanting the scaffold device of claim 1 in the subject.

19. A method of determining a toxicity or an efficacy of a therapeutically active agent, the method comprising:
    providing the device of claim 1;
    monitoring a function or activity of said cells; and
    comparing the monitored function or activity of said cells with a function or activity of said cells without the therapeutically active agent, thereby determining the toxicity or the efficacy of said therapeutically active agent to said cells.

20. The scaffold device of claim 1, wherein each electrode is individually connectable to said controller and wherein said controller is configured for applying said voltage so as to provide spatially and temporally controlled cues to said engineered tissue by said release of said agent.

* * * * *